(12) United States Patent
Wang et al.

(10) Patent No.: US 12,636,323 B2
(45) Date of Patent: May 26, 2026

(54) USE OF *CLOSTRIDIUM GHONII* COMBINED WITH TUMOR ANGIOGENESIS INHIBITOR

(71) Applicant: SHIHUIDA PHARMACEUTICAL GROUP (JILIN) CO., LTD., Baishan City (CN)

(72) Inventors: Yong Wang, Shandong (CN); Yuanyuan Liu, Shandong (CN); Wenhua Zhang, Shandong (CN); Yanqiu Xing, Shandong (CN); Shaopeng Wang, Shandong (CN); Dan Wang, Shandong (CN); Hong Zhu, Shandong (CN); Xinglu Xu, Shandong (CN); Shengbiao Jiang, Shandong (CN); Xiaonan Li, Shandong (CN); Jiahui Zheng, Shandong (CN); Rong Zhang, Shandong (CN); Dongxia Yang, Shandong (CN); Yuxia Gao, Shandong (CN); Shili Shao, Shandong (CN); Ting Han, Shandong (CN)

(73) Assignee: Shihuida Pharmaceutical Group (Jilin) Co., Ltd., Baishan City (CN)

( * ) Notice: Subject to any disclaimer, the term of this patent is extended or adjusted under 35 U.S.C. 154(b) by 345 days.

(21) Appl. No.: 18/546,553

(22) PCT Filed: Oct. 9, 2022

(86) PCT No.: PCT/CN2022/124089
§ 371 (c)(1),
(2) Date: Aug. 15, 2023

(87) PCT Pub. No.: WO2023/056972
PCT Pub. Date: Apr. 13, 2023

(65) Prior Publication Data

US 2024/0131086 A1 Apr. 25, 2024

(30) Foreign Application Priority Data

Oct. 9, 2021 (CN) .......................... 202111177878.9

(51) Int. Cl.
*A61K 35/742* (2015.01)
*A61K 31/444* (2006.01)
*A61P 35/00* (2006.01)

(52) U.S. Cl.
CPC .......... *A61K 35/742* (2013.01); *A61K 31/444* (2013.01); *A61P 35/00* (2018.01)

(58) Field of Classification Search
None
See application file for complete search history.

(56) References Cited

U.S. PATENT DOCUMENTS

2015/0147315 A1* 5/2015 Wei .......................... A61P 35/02
424/133.1

* cited by examiner

*Primary Examiner* — Brian Gangle
(74) *Attorney, Agent, or Firm* — Kinney & Lange, P.A.

(57) ABSTRACT

The present disclosure provides use of *Clostridium ghonii* combined with a tumor angiogenesis inhibitor in preparing a pharmaceutical product for treating a tumor. The present disclosure further provides a drug for treating a tumor, where the drug includes active ingredients of *Clostridium ghonii* and a tumor angiogenesis inhibitor.

6 Claims, 23 Drawing Sheets
Specification includes a Sequence Listing.

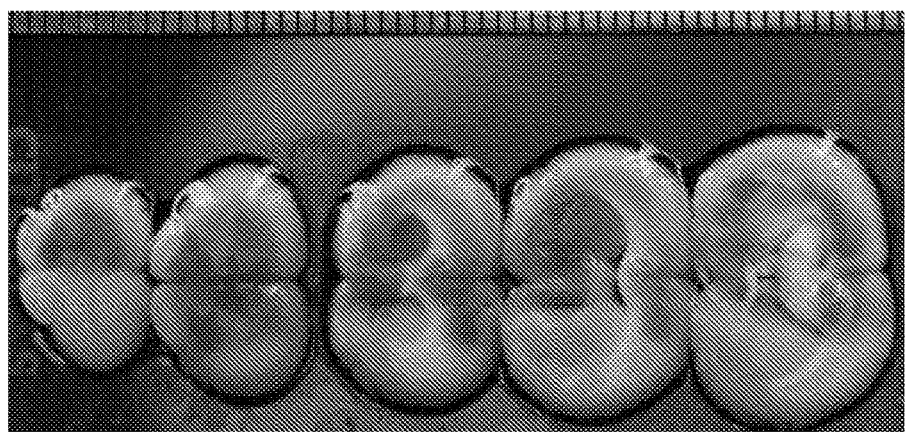
FIG. 2B
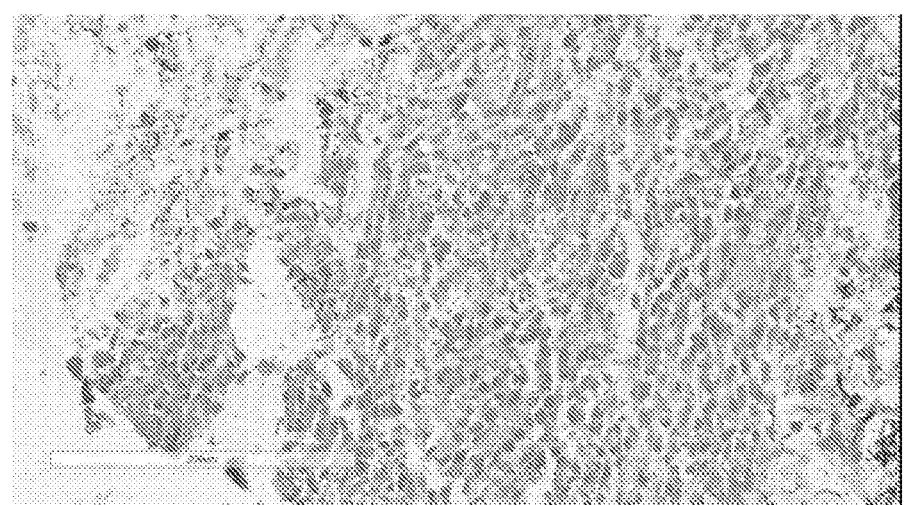
FIG. 3A
FIG. 3B

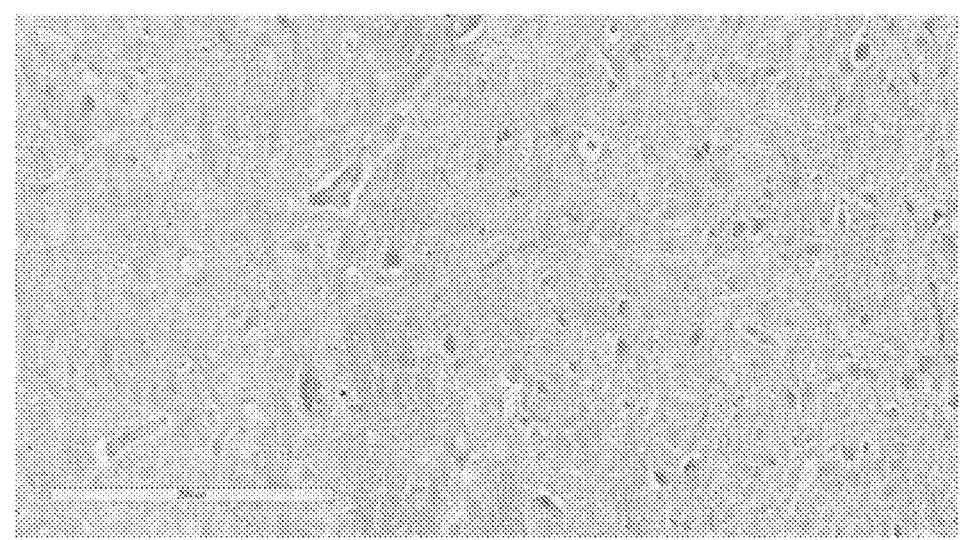
FIG. 3C
FIG. 3D
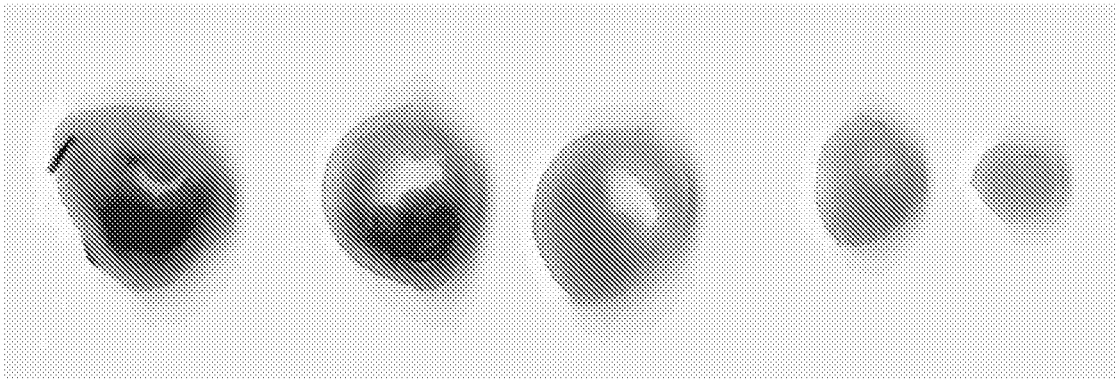
FIG. 4

- ★ Control group
- ▼ Single spore group
- ◆ *Clostridium ghonii* combined low-dose Aitan group
- ▼ Low-dose Aitan group
- ◆ *Clostridium ghonii* combined medium-dose Aitan group
- ⊖ Medium-dose Aitan group
- ⊞ *Clostridium ghonii* combined high-dose Aitan group
- △ High-dose Aitan group Single spore group

*Clostridium ghonii* combined low-dose Aitan group

Low-dose Aitan group

*Clostridium ghonii* combined medium-dose Aitan group

Medium-dose Aitan group

*Clostridium ghonii* combined high-dose Aitan group

High-dose Aitan group

Control group

Combined low-dose group

Combined high-dose group

Control group

Combined low-dose group

Combined high-dose group

SEQUENCE LISTING

```
Sequence total quantity: 2
SEQ ID NO: 1            moltype = DNA   length = 25
FEATURE                Location/Qualifiers
source                 1..25
                       mol_type = other DNA
                       note = Trx Forward primer
                       organism = synthetic construct
SEQUENCE: 1
aatacaggga attttagagg tgcag                                        25

SEQ ID NO: 2            moltype = DNA   length = 23
FEATURE                Location/Qualifiers
source                 1..23
                       mol_type = other DNA
                       note = Trx Reverse primer
                       organism = synthetic construct
SEQUENCE: 2
gctaacatct tacaaggccc aca                                          23
```

USE OF *CLOSTRIDIUM GHONII* COMBINED WITH TUMOR ANGIOGENESIS INHIBITOR

CROSS REFERENCE TO RELATED APPLICATION

The present application is a national stage application of International Patent Application No. PCT/CN2022/124089, filed on Oct. 9, 2022, which claims priority to the Chinese Patent Application No. CN202111177878.9, filed with the China National Intellectual Property Administration (CNIPA) on Oct. 9, 2021, and entitled "USE OF *CLOSTRIDIUM GHONII* COMBINED WITH TUMOR ANGIOGENESIS INHIBITOR", which is incorporated herein by reference in its entirety.

REFERENCE TO SEQUENCE LISTING

A computer readable XML file entitled "GWPCTP20230402968_seqlist", that was created on Jun. 28, 2023, with a file size of about 3,029 bytes, contains the sequence listing for this application, has been filed with this application, and is hereby incorporated by reference in its entirety.

TECHNICAL FIELD

The present disclosure belongs to the technical field of oncology, and relates to use of *Clostridium ghonii* combined with a tumor angiogenesis inhibitor, in particular to the use of the *Clostridium ghonii* combined with the tumor angiogenesis inhibitor in relieving immunosuppressive tumor microenvironment, improving tumor microenvironment and enhancing an effect of treating tumors.

BACKGROUND

Tumor microenvironment (TME) is a local steady-state environment composed of tumor cells, stromal cells, extracellular matrix and biomolecules infiltrated therein during a tumor growth process. The TME provides a material basis for tumorigenesis, development, invasion, etc., and regulates and controls biological behaviors such as tumor metastasis and relapse. Meanwhile, the TME increases drug resistance and radiation resistance of tumors, and reduces a treatment effect. Immunomodulation in the TME has an important function in tumorigenesis and development and leads to local immunosuppression in tumors through a variety of mechanisms. The TME greatly affects growth and invasion of tumors and angiognesis. Therefore, how to regulate a TME-based immunotherapy strategy and remodel an active immune microenvironment are important for an anti-tumor therapy.

Malignant tumors avoid host immune surveillance by a variety of mechanisms, including impaired lymphocyte infiltration, upregulation of immune checkpoint proteins by hypoxia, recruitment of Tregs, and establishment of an immunosuppressive tumor microenvironment that impairs functions of resident and immune effector-transporting cells. Myeloid cells infiltrated into the tumor microenvironment can regulate and control immune escape of tumor cells, tumor metastasis and other key links in tumor development.

Solid tumors are often infiltrated with a large amount of immunosuppressive agents, such as tumor-associated macrophages (TAMs), myeloid-derived suppressor cells (MDSCs) and regulatory T cells (Tregs). TGF β is essential in an immune response of the TME and capable of promoting anti-tumor immunosuppression and producing drug resistance to an anti-angiogenic therapy.

Hypoxia or low oxygen content is a typical feature of solid tumors. The hypoxia of the solid tumors can directly up-regulate an expression of an immune checkpoint protein PD-L1 of MDSCs, dendritic cells and tumor cells by HIF-1α to assist immunosuppression and escape. Meanwhile, tumor hypoxia can further increase an invasive potential of tumor cells by inducing production of mediators of cell migration (such as SDF1A and HGF) and extracellular matrix molecules of cell invasion. Hypoxia also enhances resistance of tumors to radiotherapy and chemotherapy.

*Clostridium ghonii* is an obligate anaerobe, and can only specifically germinate and multiply in tumor hypoxia or necrosis areas, effectively dissolve tumor tissues regardless of their types and destroy the TME. After oncolysis by *Clostridium ghonii*, immunogenicity of the TME is changed, the immunosuppressive TME is adjusted, and an anti-tumor immune response is induced. At present, there are no relevant reports that the *Clostridium ghonii* combined with the tumor angiogenesis inhibitor can significantly change the immunosuppressive TME and enhance the anti-tumor effect.

SUMMARY

Aiming at the deficiencies of the prior art, the present disclosure provides use of a safer and highly targeted anaerobic bacterium-*Clostridium ghonii* combined with a tumor angiogenesis inhibitor in treating solid tumors.

Use of *Clostridium ghonii* combined with a tumor angiogenesis inhibitor in preparing a pharmaceutical product for treating a tumor is provided.

A drug for treating a tumor is provided, where the drug includes an active ingredient of a *Clostridium ghonii* and a tumor angiogenesis inhibitor.

According the present disclosure, preferably, the *Clostridium ghonii* may be a *Clostridium ghonii* MW-DCG-LCv-26 strain or a strain obtained after domestication of the *Clostridium ghonii*; the *Clostridium ghonii* MW-DCG-LCv-26 is deposited in the National Measurement Institute, Australia and has a date of deposit of Apr. 18, 2012 and a deposit number of V12/001486; and the strain obtained after domestication of the *Clostridium ghonii* includes an MW-DCG-HNCv-18 bacterial strain or an MW-DCG-CCv-17 bacterial strain. The MW-DCG-HNCv-18 strain is deposited in the National Measurement Institute, Australia, with a date of deposit of Apr. 18, 2012 and a deposit number of V12/001485; and the MW-DCG-CCv-17 strain is deposited in the National Measurement Institute, Australia, and has a date of deposit of Apr. 18, 2012 and a deposit number of V12/001487.

According the present disclosure, preferably, the *Clostridium ghonii* may be in a spore form.

According the present disclosure, preferably, the tumor angiogenesis inhibitor may be one or a combination of two or more selected from the group consisting of apatinib (AITAN), sunitinib, pazopanib, bevacizumab, ramucirumab, conbercept, aflibercept, sorafenib, and regorafenib.

According the present disclosure, preferably, the active ingredient of the *Clostridium ghonii* and the tumor angiogenesis inhibitor may be administrated successively or simultaneously.

According the present disclosure, preferably, every $1 \times 10^7$ CFU of the *Clostridium ghonii* spore freeze-dried powder may be combined with apatinib (AITAN) at an optimal dose of 60 mg/kg/d.

According the present disclosure, preferably, the tumor may include but be not limited to colon cancer, Lewis lung carcinoma, nasopharyngeal cancer, non-small cell lung cancer, fibrosarcoma, melanoma, etc.

In the present disclosure, the tumor angiogenesis inhibitor can be randomly used in combination. *Clostridium ghonii* spores must be pure, that is, do not include any other bacteria and the tumor angiogenesis inhibitor should also be sterile. The *Clostridium ghonii* spores are prepared and purified according to an existing method in the art to obtain a drug that meets relevant quality standards.

Beneficial Effects

1. The present disclosure discovers a safer and highly targeting *Clostridium ghonii* combined with a tumor angiogenesis inhibitor in efficiently preventing tumors for the first time.
2. It is found for the first time that the *Clostridium ghonii* combined with a low-dose tumor angiogenesis inhibitor relieves infiltration of M2-like macrophages, myeloid-derived suppressor cells (MDSCs) and the like in tumors, and reduces the number of TGF-β in the tumors and an inhibition effect of an anti-tumor immune response in a tumor microenvironment (TME). Meanwhile, the combination with the low-dose tumor angiogenesis inhibitor can promote infiltration of immune cells such as CD8$^+$, CD3$^+$ T and F4/80$^+$ into tumors, improves the immune microenvironment in the tumors and enhances an anti-tumor curative effect.
3. The present disclosure determines an optimal dose of the tumor angiogenesis inhibitor combined with the *Clostridium ghonii*.
4. The *Clostridium ghonii* combined with the tumor angiogenesis inhibitor can be used in advanced malignant solid tumors. The *Clostridium ghonii* combined with low-dose AITAN (apatinib) reduces the inhibition effect of the anti-tumor immune response in the TME, converts an immunosuppressive state of the TME into an immune-activated state and efficiently prevent tumors. A unique treatment effect is attributed to a change of an anti-tumor immune microenvironment instead of creating an anoxic environment for breeding *Clostridium ghonii* by high-dose AITAN (apatinib) to aggravate tumor hypoxia.
5. A composition of the present disclosure is safer and more targeted in treating tumors, can only germinate in a tumor hypoxic environment, but cannot germinate into bacteria in a non-tumor hypoxic environment.

BRIEF DESCRIPTION OF THE DRAWINGS

FIGS. 2A-2B show TTC staining of cerebral infarction tissues in example 2;

FIGS. 3A-3D show Gram stain of tissue sections in example 2;

FIG. 4 shows TTC staining of myocardial infarction tissues in example 2;

DETAILED DESCRIPTION OF THE EMBODIMENTS

Figure 1:
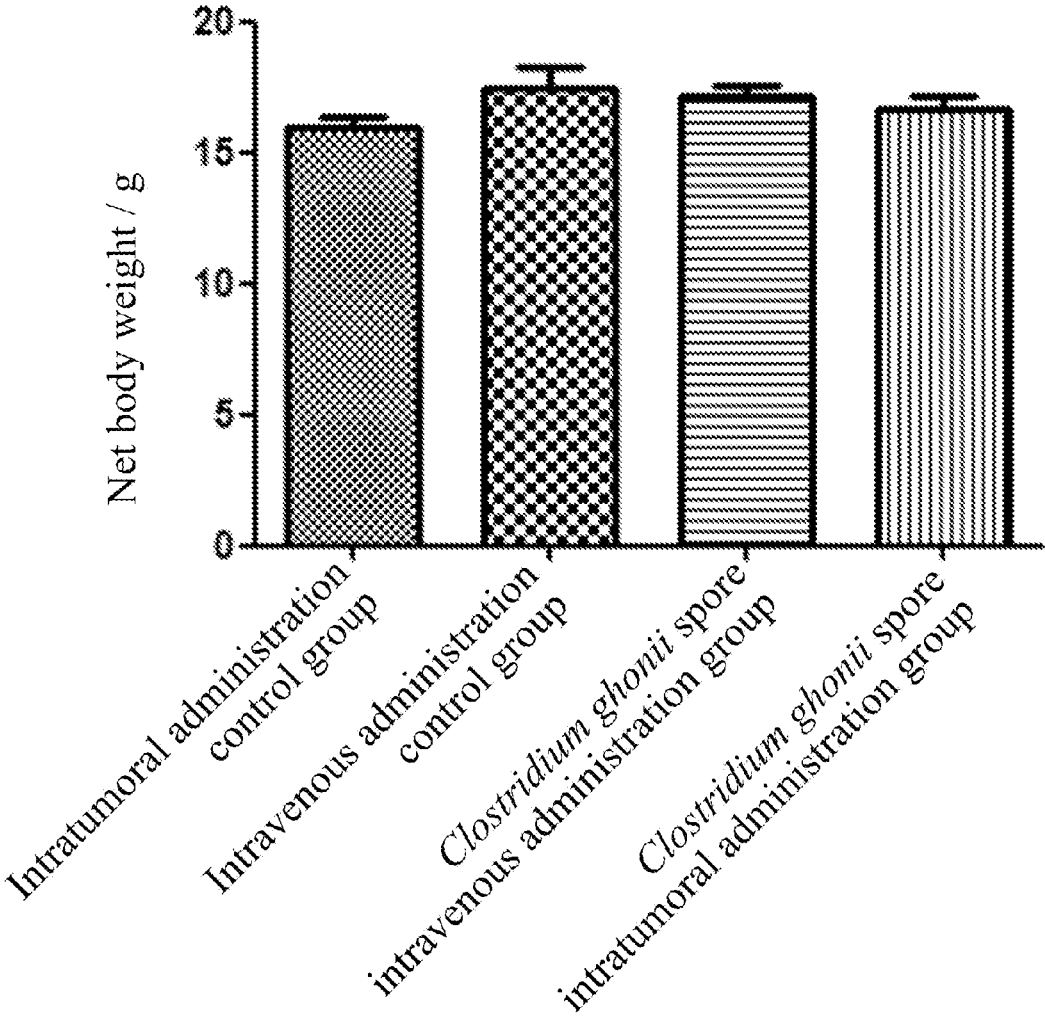
FIG. 1 is a histogram showing net body weight in example 2.

The present disclosure will be further described in detail below in conjunction with specific examples. The described examples are only a part of technical solutions listed in the present disclosure for the convenience of the public to understand. These examples are only used to illustrate the present disclosure and not to limit the protection scope of the present disclosure. The protection scope of the present disclosure is defined by the claims.

Example 1

Materials and Methods

*Clostridium ghonii* Spore Freeze-Dried Powder

*Clostridium ghonii* spore freeze-dried powder for injection: an MW-DCG-LCv-26 strain was deposited in the National Measurement Institute, Australia, had a date of deposit of Apr. 18, 2012 and a deposit number of V12/001486 and a batch number of 202003001-1, and was developed by Shandong Xinchuang Biotechnology Co., Ltd. The *Clostridium ghonii* spore freeze-dried powder for injection was prepared from *Clostridium ghonii* spores as an active ingredient and 1% sucrose as an auxiliary material, and prepared by a freeze-drying procedure of freezing at −40° C. for 4 h, vacuumizing at −35° C. for 10 min; and freeze-drying at −30° C. for 10 min, −25° C. for 10 min, −20° C. for 26 h, −15° C. for 2 h, −10° C. for 10 min, −5° C. for 10 min, 0° C. for 10 min, 10° C. for 2 h, 15° C. for 10 min, 20° C. for 3 h and 27° C. for 3 h, and had a specification of 1×10$^8$ CFU/bottle; reference substance freeze-dried powder had a batch number of 201910002F, and was developed by Shandong Xinchuang Biotechnology Co., Ltd., and prepared from 1 mL of 1% sucrose solution through the above freeze-drying procedure; a 0.9% sodium chloride injection had a batch number of 2005062146 and was commercially available in CISEN Pharmaceutical Co., LTD.; and sterile water for injection had a batch number of 1902212162 and was commercially available in CISEN Pharmaceutical Co., LTD.

Cell Line and Cell Culture

CT26.WT colon cancer cells had a number of 3131C0001000800037 and were deposited in Cell Resource Center, Shanghai Institutes for Biological Sciences, Chinese Academy of Sciences. Special-grade fetal bovine serum at a volume percentage of 10% (there may be floating matter in the serum after low-temperature thawing and the serum was centrifuged at 2,000 rpm for 3 min to remove the floating matter) and a penicillin-streptomycin mixture at a volume percentage of 1.1% were added into a RPMI Medium 1640 basic medium to be mixed fully and evenly, cells were resuspended, a cell suspension was inoculated into a 75-cm$^2$ cell culture flask, 25 mL of a cell culture medium was added into each flask, and the cells were placed in a 5% CO$_2$ cell incubator for static culture at 37° C.

Reagent

The RPMI Medium 1640 basic medium was purchased from Gibco, the special-grade fetal bovine serum and the penicillin-streptomycin mixture were purchased from BI, AITAN (apatinib) was purchased from Jiangsu Hengrui Pharmaceuticals Co., Ltd., and the *Clostridium ghonii* spores were prepared and purified according to an existing method in the art to obtain a drug that met relevant quality standards.

Establishment of Models

BALB/c mice were subcutaneously inoculated with CT26 tumor cells to establish a subcutaneous tumor model for colon cancer. 0.2 mL of a cell suspension with a concentration of 7.5×10$^6$ cells/mL (acceptable range: 6.75×10$^6$ cells/mL-8.25×10$^6$ cells/mL) was extracted with a 1-mL disposable sterile syringe and slowly subcutaneously injected into axillae of right forelimbs of mice (pre-sterilized with 75% alcohol). After injection, needle eyes were gently pressed with dry cotton balls.

Observation and Examination

Clinical observation: during an administration period, animal behaviors, death or near-death, etc. were observed using the naked eyes once every morning and afternoon.

Tumor measurement: a maximum long diameter (L) and a maximum transverse diameter (W) of a tumor (including a thickness of a mouse skin) were measured with a vernier caliper, and a tumor volume was calculated according to a formula of $$V = \frac{L \times W^2}{2}.$$

Body weight: during the administration period, body weight was measured on the day of the tumor measurement from the day of treatment.

Tumor weight: a tumor tissue was dissected out and weighed and tumor weight was recorded.

Tumor inhibition rate (IR$_{TW}$%)=(average tumor weight of control group-average tumor weight of experimental group)/average tumor weight of control group×100%.

Analysis by Flow Cytometry

Tumors and spleens in the model for colon cancer were collected at the corresponding time and digested at 37° C. for 1 h in a DMEM medium containing type IV collagenase (1 mg/mL, Sigma), hyaluronidase (1 mg/mL, Sigma) and DNaseI (20 U/mL, Sigma). Single tumor cells and spleen cells were collected. The isolated single cells were individually washed with PBS containing 2% FCS and surface-stained with a relevant antibody. After the cells were extensively washed, data were acquired by a BD FACS Calibur (Becton Dickinson). The data of flow cytometry were analyzed by NovoExpress™ (ACEA Biosciences, Inc.).

Detection of Cytokines by Multi-ELISA

The peripheral blood and tumor tissues of the experimental mice were collected. Cytokines such as IL-10, TNF-α, GM-CSF and TGFβ were evaluated. A Multi-ELISA kit was purchased from Qiagen (Australia) and an experiment was performed according to the instructions provided in the kit.

Results of ELISA were read at 450 nm on ELISA microplates (Polarstar Omega 96-well microplatereader BMG Labtech GmBH, Germany).

TCC Staining

After the tumor tissue was quick-frozen in liquid nitrogen, the tissue was uniformly cut into 5 slices with a same thickness using a microtome knife. The tumor tissue sections were placed on glass slides, 2% TTC solution was added dropwise to cover the tissue sections, a reaction was performed in the dark for 30 min, and photographing was performed with a digital camera.

Immunohistochemistry Staining

The tumor tissue was quickly fixed in a 10% neutral formalin solution, the fixed tissue was embedded in paraffin, and the embedded tissue was sectioned. The paraffin sections were dewaxed and rehydrated. The sections were incubated in 3% H$_2$O$_2$ deionized water for 10 min at a room temperature in the dark to block endogenous peroxidase activity and rinsed with PBS 3 times for 5 min each time. The sections were immersed into an EDTA repair solution (1×) and heated to be boiled out using a microwave oven, power was cut off, and the sections were repaired 1-2 times at intervals of 5-10 min and cooled. A 5% BSA blocking solution was added dropwise onto the sections and the sections were incubated at 37° C. for 30 min and spin-dried. Properly diluted primary mouse monoclonal Anti-CD163 and HIF-1α antibodies were added dropwise onto the sections, and the sections were incubated at 37° C. for 1-2 h or at 4° C. overnight. The sections were rinsed 3 times with PBS for 5 min each time. A biotin-labeled goat anti-rabbit IgG secondary antibody was added dropwise onto the sections and the sections were incubated at 37° C. for 30 min. The sections were rinsed 3 times with PBS for 5 min each time. SABC was added dropwise onto the sections and the sections were incubated at 37° C. for 30 min. The sections were rinsed 3 times with PBS for 5 min each time. Each 1 drop of chromogenic reagents A, B and C was added to 1 mL of distilled water to be mixed evenly, an obtained mixture was added to the specimen sections for developing for 1-10 min, and washing was conducted with distilled water to terminate a reaction. Hematoxylin counterstaining was conducted. The stained sections were dehydrated until transparent. After mounted with a neutral gum, the sections were observed under a microscope.

Gram Stain of Tumor Tissue Sections

The tumor tissue was quickly fixed in a 10% neutral formalin solution, the fixed tissue was embedded in paraffin, and the embedded tissue was sectioned. The sections were baked for 30 min, the baked sections were soaked with xylene I for 5 min, xylene II for 5 min, 100% ethanol I for 2 min, 95% ethanol I for 2 min and 80% ethanol I for 2 min, and the soaked sections were rinsed with running water and air-dried; the sections were covered with Gram reagent I for 1 min and rinsed with running water, covered with Gram reagent II for 1 min and rinsed with running water, covered with gram reagent III for about 20 s and rinsed with running water, and stained with eosin for about 20 s and rinsed with running water; the sections were soaked with 95% ethanol II for 30 s, 95% ethanol III for 1 min, 100% ethanol II for 2 min, xylene III for 3 min and xylene IV for 3 min, and the soaked sections were mounted with a neutral gum and observed.

Quantitative Analysis of *Clostridium ghonii*

Tissue RNA was extracted by a Trizol method and the RNA was reverse transcribed into cDNA using a PrimeScript™ RT reagent Kit with gDNA Eraser (Perfect real time) kit. The cDNA was used as a template and specific primers for *Clostridium ghonii* thioredoxin were used to detect *Clostridium ghonii*. The primer sequences were as follows:

```
Trx Forward primer (SEQ ID NO: 1):
5'-AATACAGGGAATTTTAGAGGTGCAG-3'

Trx Reverse primer (SEQ ID NO: 2):
5'-GCTAACATCTTACAAGGCCCACA-3'
```

Statistical Analysis

Statistical analysis was conducted with a two-tailed t-test or a Mann-Whitney test using Prism 6.0 (Graphpad Software, SanDiego). $p < 0.05$ indicates that the difference is statistically significant.

Example 2

High Safety and Strong Targeting of Use of *Clostridium ghonii* in Models for Solid Tumor Establishment of Models A subcutaneous xenograft model for colon cancer was established. A middle cerebral artery occlusion (MCAO) model was established in SD rats. An acute myocardial infarction (MI) model was established in C57BL/6 mice.

Animal Grouping

On the day of screening tumor-bearing animals, experimental animals with a tumor volume of 0.35-0.60 $cm^3$ were selected for an experiment. According to a random principle, the screened conforming animals were divided into 4 groups by lottery: intravenous administration control group, intratumoral administration control group, *Clostridium ghonii* spore intravenous administration group, *Clostridium ghonii* spore intratumoral administration group, with 8 mice in each group.

In the middle cerebral artery occlusion (MCAO) model in SD rats, the rats were randomly divided into 4 groups: healthy rat control group, cerebral infarction model control group, cerebral infarction model intravenous administration group, cerebral infarction model intracranial administration group, with 5 rats in each group.

In the acute myocardial infarction (MI) model in C57BL/6 mice, the mice were randomly divided into 3 groups: myocardial infarction model TTC staining group, myocardial infarction model control group and myocardial infarction model tail vein administration group, with 5 mice in each group.

Administration

The model for colon cancer: the mice were intratumorally administrated with a spore dose of $1 \times 10^7$ cfu/tumor/time in the *Clostridium ghonii* spore intratumoral administration group and a same volume of an sodium chloride injection at a mass/volume percent concentration of 0.9% in the intratumoral administration control group; and the mice were administrated via a tail vein with a spore dose of $1 \times 10^8$ cfu/tumor/time in the *Clostridium ghonii* spore intravenous administration group and a same volume of an sodium chloride injection at a mass/volume percent concentration of 0.9% in the intravenous administration control group.

The middle cerebral artery occlusion (MCAO) model in SD rats: a dose of a tail vein administration was $5 \times 10^7$ CFU and a dose of an intracranial administration was $1 \times 10^6$ CFU.

The acute myocardial infarction (MI) model in C57BL/6 mice: a dose of a tail vein administration was $2 \times 10^7$ CFU.

Observation and Examination

During the experiment of the model for colon cancer, death or near-death, behaviors, and body weight of the mice were observed.

For the MCAO model and the MI model, brain tissues and heart tissues were taken separately for TTC staining, qPCR of *Clostridium ghonii*, spore culture detection, and the tissue sections was subjected to Gram stain of *Clostridium ghonii*.

Results

During the experiment, the mice subjected to intratumoral or intravenous administration in the model for colon cancer were all alive. There was no significant difference in the net body weight of the mice in the *Clostridium ghonii* spore administration groups compared with the control groups (FIG. 1).

Figure 2A:
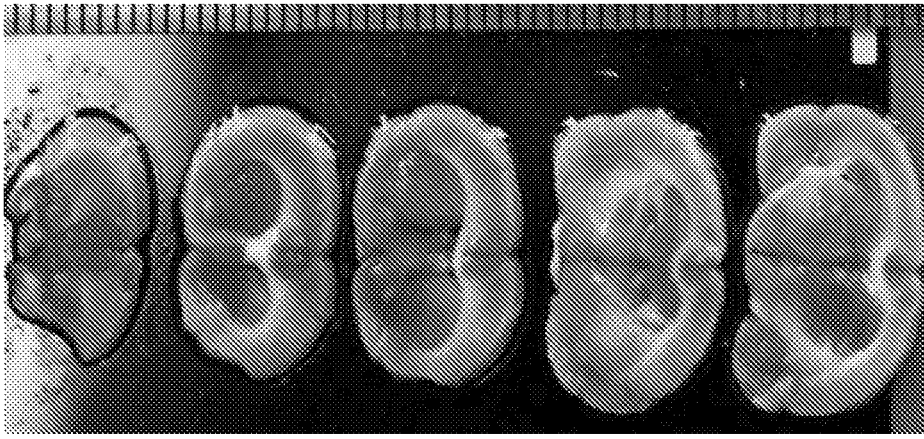

In the experiment of the MCAO model, brain tissues of the rats in the healthy rat control group, the cerebral infarction model control group, the cerebral infarction model intravenous administration group, the cerebral infarction model intracranial administration group were subjected to TTC staining. The TTC staining showed that the brain tissue sections of healthy rats were red, and a part of a brain tissue area of the rats suffered from cerebral infarction was pale white in the brain tissue sections of the rats in the MCAO model (FIG. 2A and FIG. 2B).

Detection of *Clostridium ghonii* and spores were conducted in the brain tissues in the experiment of the MCAO model. *Clostridium ghonii* spores were detected in the brain tissues of cerebral infarction, but *Clostridium ghonii* was not detected after a single tail vein administration of *Clostridium ghonii* spores for injection and a single intracranial administration of *Clostridium ghonii* spores for injection.

The brain tissues were sectioned and Gram stained. The stained brain tissue sections of the rats in each group were scanned by a digital pathology system to detect distribution of *Clostridium ghonii*. Short rod-shaped and blue-purple *Clostridium ghonii* was showed in tumor tissue sections with *Clostridium ghonii* (positive control) after Gram stain (FIG. 3A); no *Clostridium ghonii* was showed in tumor tissue sections without *Clostridium ghonii* (negative control) after Gram stain (FIG. 3B); and *Clostridium ghonii* was not detected in the brain tissue sections of cerebral infarction after a single tail vein administration of *Clostridium ghonii* spores for injection and a single intracranial administration of *Clostridium ghonii* spores for injection after artery occlusion of rat brains (FIGS. 3C and 3D).

TTC staining showed that a myocardial tissue of the mice in the MI model TTC staining group was white, indicating that the mice in the MI model suffered from an obvious infarction (FIG. 4). *Clostridium ghonii* spores were detected in the myocardial tissues of myocardial infarction, but *Clostridium ghonii* was not detected after a single tail vein administration of *Clostridium ghonii* spores for injection in the mice of the MI model.

Figures 5, 6:
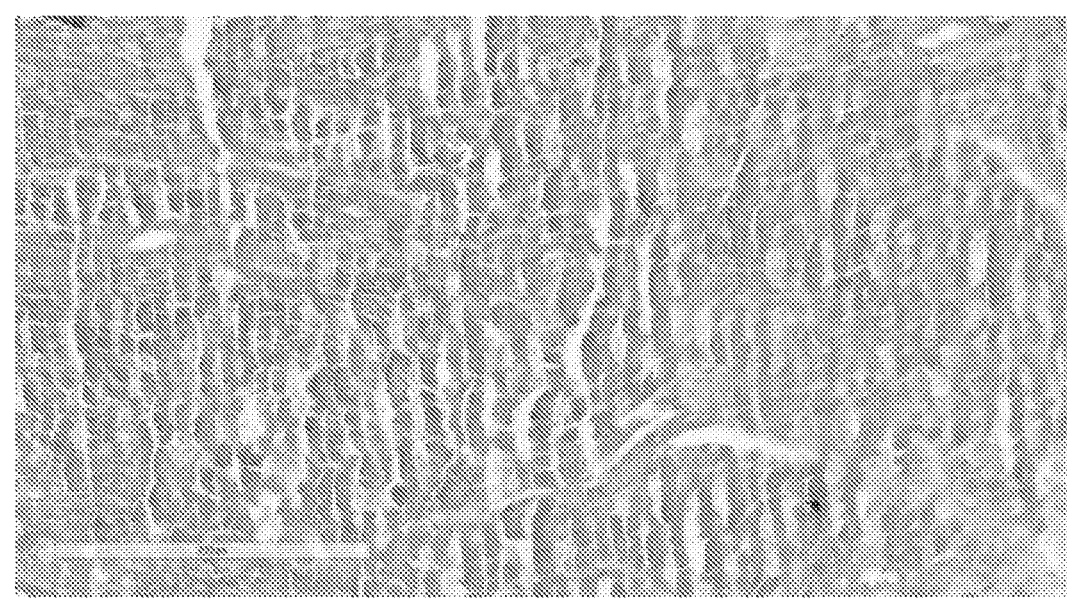
FIG. 5 shows Gram staining of tissue sections in example 2.
FIG. 6 is a histogram showing net body weight of experimental mice in example 3.

The heart tissues were sectioned and Gram stained. The stained heart tissue sections of the mice in each group were scanned by a digital pathology system to detect distribution of *Clostridium ghonii*. Short rod-shaped and blue-purple *Clostridium ghonii* was showed in tumor tissue sections of a positive control group after Gram stain (FIG. 3A); no *Clostridium ghonii* was showed in tumor tissue sections of a negative control group after Gram stain (FIG. 3B); and *Clostridium ghonii* was not detected in the myocardial tissues of myocardial infarction after a single tail vein administration of *Clostridium ghonii* spores for injection in the mice of the MI model (FIG. 5).

Example 3

Antitumor Effect of *Clostridium ghonii* Spores Combined with Different Doses of Apatinib (AITAN) in CT26 Mouse Model According to a random principle, the conforming mice (a tumor volume of 0.31-0.41 cm$^3$) were divided into 8 groups by lottery: control group, spore group, high-dose apatinib (AITAN) group, medium-dose apatinib (AITAN) group, low-dose apatinib (AITAN) group, *Clostridium ghonii* combined low-dose apatinib (AITAN) group, *Clostridium ghonii* combined medium-dose apatinib (AITAN) group, and *Clostridium ghonii* combined high-dose apatinib (AITAN) group.

Control group: the mice were intratumorally administrated with a same volume of a 0.9% sodium chloride injection;

spore group: the mice were intratumorally administrated at a dose of 1×10$^7$ cfu/tumor/time twice;

High-dose apatinib (AITAN) group: the mice were gavaged at a dose of 180 mg/kg/d once every day for a total of 7 times;

Medium-dose apatinib (AITAN) group: the mice were gavaged at a dose of 120 mg/kg/d once every day for a total of 7 times;

Low-dose apatinib (AITAN) group: the mice were gavaged at a dose of 60 mg/kg/d once every day for a total of 7 times; and

*Clostridium ghonii* combined apatinib (AITAN) groups: mice were first intratumorally administrated with apatinib (AITAN) once every day for 3 days and then *Clostridium ghonii* spores at a dose of 1×10$^7$ cfu/tumor/time once every other day for a total of two times. The dose of the apatinib (AITAN) in the combined high, medium and low-dose apatinib (AITAN) groups was the same as that in the high, medium and low-dose apatinib (AITAN) groups.

Results

During a treatment period, there was no death or near-death of the mice in each group. Before treatment, there was no significant difference in body weight of mice in each group (all p>0.05). There was no significant difference in the net body weight of the mice in each group compared with the control group (all p>0.05). The net body weight of the tumor-bearing mice was shown in Table 1 and FIG. 6.

TABLE 1

| | Net body weight of experimental mice | | | |
| --- | --- | --- | --- | --- |
| Group | Control group (n = 7) | Single spore group (n = 7) | *Clostridium ghonii* combined low-dose apatinib (AITAN) group (n = 7) | Low-dose apatinib (AITAN) group (n = 7) |
| Net body weight (g) | 17.66 ± 1.22 | 16.06 ± 1.01 | 16.16 ± 1.74 | 18.32 ± 1.12 |
| Group | *Clostridium ghonii* combined apatinib (AITAN) medium-dose group (n = 7) | Medium-dose apatinib (AITAN) group (n = 7) | *Clostridium ghonii* combined apatinib (AITAN) high-dose group (n = 7) | High-dose apatinib (AITAN) group (n = 7) |
| Net body weight (g) | 17.18 ± 0.78 | 18.02 ± 1.61 | 16.12 ± 0.72 | 18.44 ± 1.42 |

Note:

n is the number of experimental animals in each group and the net body weight of mice is the body weight of the mice after tumor-bearing mice were excised. The data are mexpressed as mean ± standard deviation.

Figure 7:
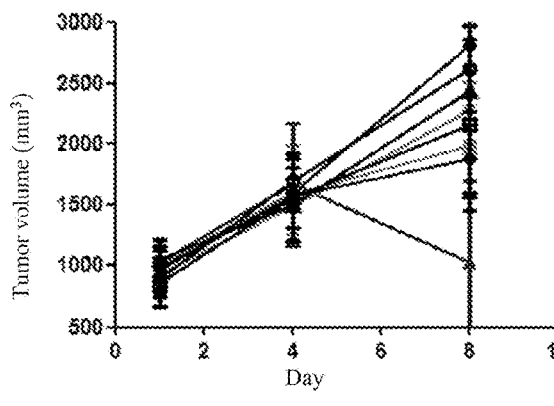
FIG. 7 is a curve graph showing tumor volumes of experimental mice in example 3.

Before treatment, there was no significant difference in tumor volume of the tumor-bearing mice in each group (all p>0.05). At the end of administration, compared with the control group, the tumor volume of mice in the single spore group, the *Clostridium ghonii* combined low-dose apatinib (AITAN) group, and the *Clostridium ghonii* combined medium-dose apatinib (AITAN) group was significantly smaller than that of the mice in the control group (p=0.045, p=0.000 and p=0.026). The tumor volume of the tumor-bearing mice was shown in Table 2 and FIG. 7.

TABLE 2

| | | | | |
|---|---|---|---|---|
| | | | Tumor volume of tumor-bearing mice | |
| Day | Control group (mm³) (n = 7) | Single spore group (mm³) (n = 7) | *Clostridium ghonii* combined low-dose apatinib (AITAN) group (mm) (n = 7) | Low-dose apatinub (AITAN) group (mm) (n = 7) |
| D-1 | 996.37 ± 130.93 | 1023.59 ± 200.27 | 1026.03 ± 97.91 | 931.50 ± 97.91 |
| D-4 | 1606.25 ± 291.83 | 1584.84 ± 401.26 | 1669.35 ± 504.54 | 1489.82 ± 232.84** |
| D-8 | 2813.11 ± 416.55 | 1982.64 ± 533.59* | 1025.99 ± 676.02 | 2275.35 ± 348.84 |
| Day | Control group (mm³) (n = 7) | Single spore group (mm³) (n = 7) | *Clostridium ghonii* combined low-dose apatinib (AITAN) group (mm³) (n = 7) | Low-dose apatinib (AITAN) group (mm³) (n = 7) |
| D-1 | 968.47 ± 198.03 | 892.74 ± 156.30 | 865.43 ± 198.95 | 1049.42 ± 166.37 |
| D-4 | 1573.97 ± 357.26 | 1698.84 ± 177.49 | 1566.05 ± 359.30 | 1499.45 ± 303.10 |
| D-8 | 1880.47 ± 279.87* | 2615.77 ± 351.13 | 2160.22 ± 704.11 | 2442.80 ± 882.95 |

Note:

n is the number of experimental animals in each group. The data are expressed as mean ± standard deviation. Compared with the control group, *p < 0.05 and **p < 0.01.

Note: n is the number of experimental animals in each group. The data are expressed as mean±standard deviation. Compared with the control group, *p<0.05 and **p<0.01.

Figure 8:
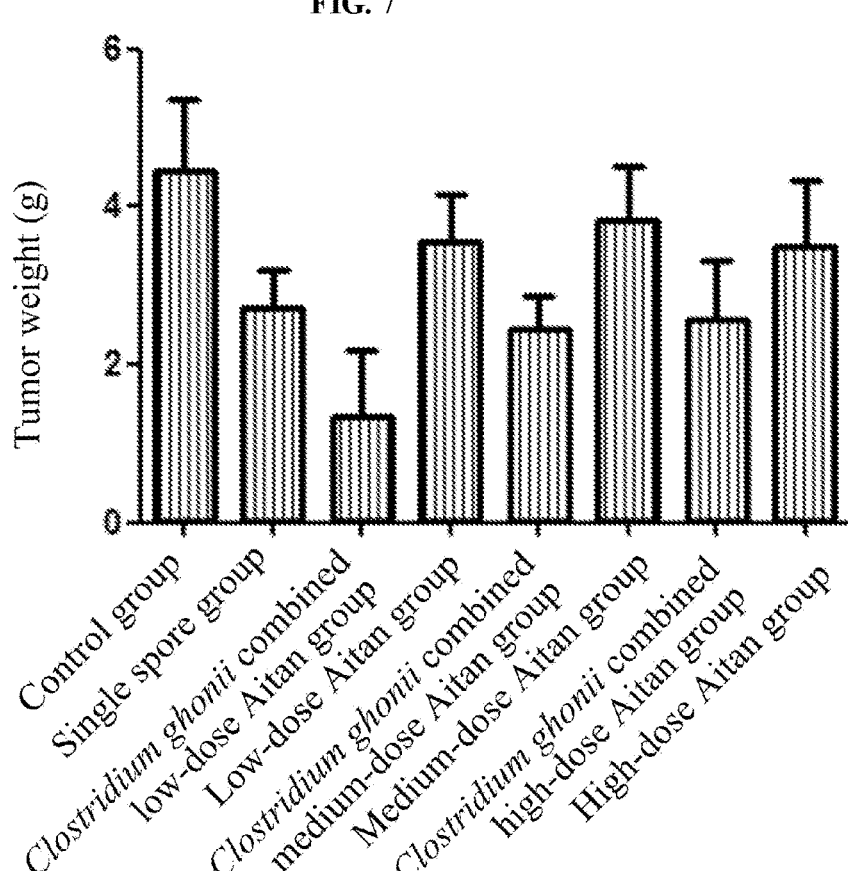
FIG. 8 is a histogram showing tumor weight of experimental mice in example 3.
Figure 9A:
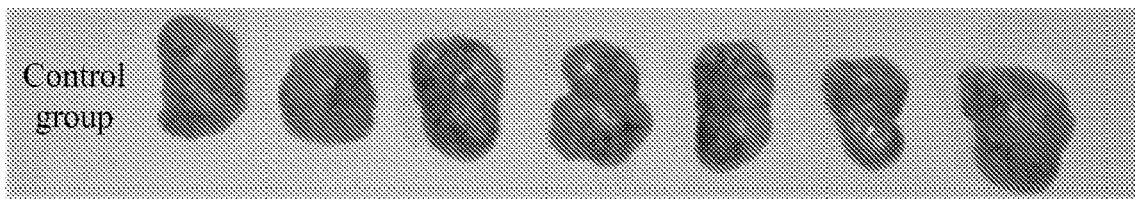
FIGS. 9A-H show anatomical tumor diagrams of experimental mice in example 3.
Figures 9B, 9C, 9D, 9E, 9F, 9G, 9H:
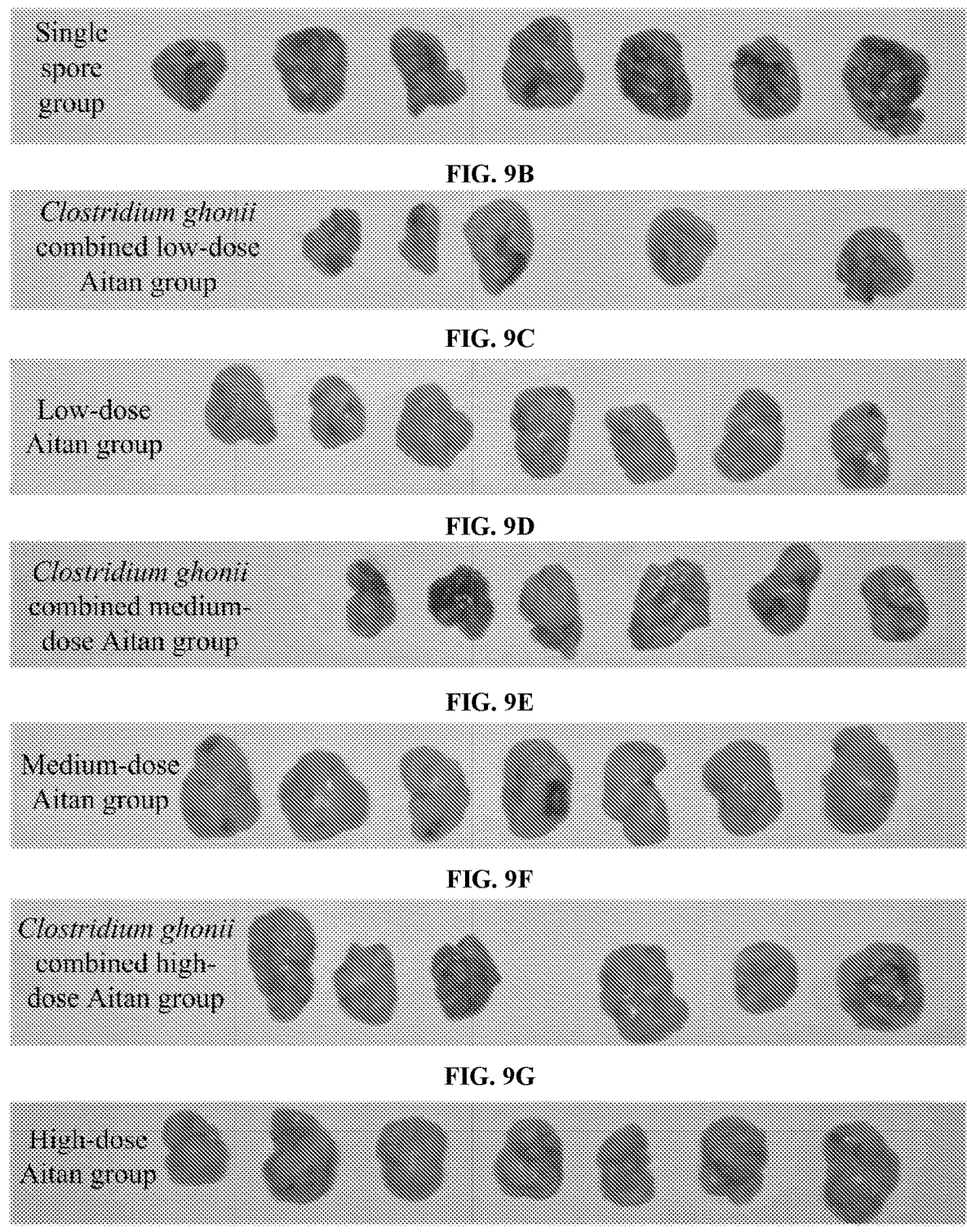

The tumor weight in the single spore group, *Clostridium ghonii* combined low-dose apatinib (AITAN) group, *Clostridium ghonii* combined medium-dose apatinib (AITAN) group and *Clostridium ghonii* combined high-dose apatinib (AITAN) group was significantly lower than that in the control group (p=0.000, p=0.000, p=0.000 and p=0.000). The tumor weight of mice in each group was shown in Table 3 and FIG. 8.

TABLE 3

| | | | | |
|---|---|---|---|---|
| | | | Tumor weight | |
| Group | Control group (n = 7) | Single spore group (n = 7) | *Clostridium ghonii* combined low-dose apatinib (AITAN) group (n = 7) | Low-dose apatinib (AITAN) group (n = 7) |
| Tumor weight (g) | 4.45 ± 0.92 | 2.72 ± 0.48** | 1.33 ± 0.84** | 3.55 ± 0.61 |
| Group | *Clostridium ghonii* combined medium-dose apatinib (AITAN) group (n = 7) | Medium-dose apatinib (AITAN) group (n = 7) | *Clostridium ghonii* combined apatinib (AITAN) high-dose group (n = 7) | High-dose apatinib (AITAN) group (n = 7) |
| Tumor weight (g) | 2.46 ± 0.41** | 3.84 ± 0.69 | 2.58 ± 0.76** | 3.49 ± 0.86 |

The tumor inhibition rate was calculated according to the tumor weight. The tumor inhibition rate of each group was: *Clostridium ghonii* combined low-dose apatinib (AITAN) group>*Clostridium ghonii* combined medium-dose apatinib (AITAN) group>*Clostridium ghonii* combined high-dose group>single spore group>high-dose apatinib (AITAN) group>low-dose apatinib (AITAN) group>medium-dose apatinib (AITAN) group as shown in Table 4. Anatomy photos of tumors were shown in FIGS. 9A-H.

TABLE 4

| | | | | |
|---|---|---|---|---|
| | | | Tumor inhibition rate | |
| Group | Control group (n = 7) | Single spore group (n = 7) | *Clostridium ghonii* combined low-dose apatinib (AITAN) group (n = 7) | Low-dose apatinib (AITAN) group (n = 7) |
| Anti-bacterial rate (%) | / | 38.97 | 70.07 | 20.21 |
| Group | *Clostridium ghonii* combined medium-dose apatinib (AITAN) group (n = 7) | Medium-dose apatinib (AITAN) group (n = 7) | *Clostridium ghonii* combined high-dose apatinib (AITAN) group (n = 7) | High-dose apatinib (AITAN) group (n = 7) |
| Anti-bacterial rate (%) | 44.70 | 13.89 | 42.12 | 21.68 |

28.6% of mouse tumors in the mice in the *Clostridium ghonii* combined low-dose apatinib (AITAN) group were completely eliminated and no tumor growth was shown at the end of the experiment. The mice in the *Clostridium ghonii* combined low-dose apatinib (AITAN) group had a cure rate significantly higher than that in the *Clostridium ghonii* combined high-dose apatinib (AITAN) group (14.3%) and *Clostridium ghonii* combined medium-dose apatinib (AITAN) group (14.3%). However, the tumors were not eliminated in the high, medium and low-dose apatinib (AITAN) group and single spore group and the cure rate was 0% in those groups. It can be seen that *Clostridium ghonii* combined with low-dose apatinib (AITAN) showed a significant anti-tumor effect which was significantly better than that of other groups as shown in Table 5.

TABLE 5

| | | | | |
|---|---|---|---|---|
| | | | Cure rate | |
| Group | Control group (n = 7) | Single spore group (n = 7) | *Clostridium ghonii* combined low-dose apatinib (AITAN) group (n = 7) | Low-dose apatinib (AITAN) group (n = 7) |
| Cure rate (%) | 0 | 0 | 28.6 | 0 |
| Group | *Clostridium ghonii* combined apatinib (AITAN) medium-dose group (n = 7) | Medium-dose apatinib (AITAN) group (n = 7) | *Clostridium ghonii* combined apatinib (AITAN) high-dose group (n = 7) | High-dose apatinib (AITAN) group (n = 7) |
| Cure rate (%) | 14.3 | 0 | 14.3 | 0 |

It can be seen from the above results that each-dose treatment showed an inhibitory effect on tumor growth and the *Clostridium ghonii* combined with the low-dose apatinib (AITAN) had a most obvious anti-tumor effect. The combined treatment of the *Clostridium ghonii* spores and the anti-angiogenic inhibitor such as apatinib (AITAN) showed a super-additive effect and the *Clostridium ghonii* combined with the low-dose apatinib (AITAN) had a best anti-tumor effect.

Example 4

Study on Anti-Tumor Mechanism of *Clostridium ghonii* Combined with High-Dose and Low-Dose Apatinib (AITAN)

The *Clostridium ghonii* combined with low-dose apatinib (AITAN) had an obviously better anti-tumor effect than the *Clostridium ghonii* combined with high-dose apatinib (AITAN). An anti-tumor mechanism of the *Clostridium ghonii* combined with high-dose and low-dose apatinib (AITAN) was studied.

Figure 10A:
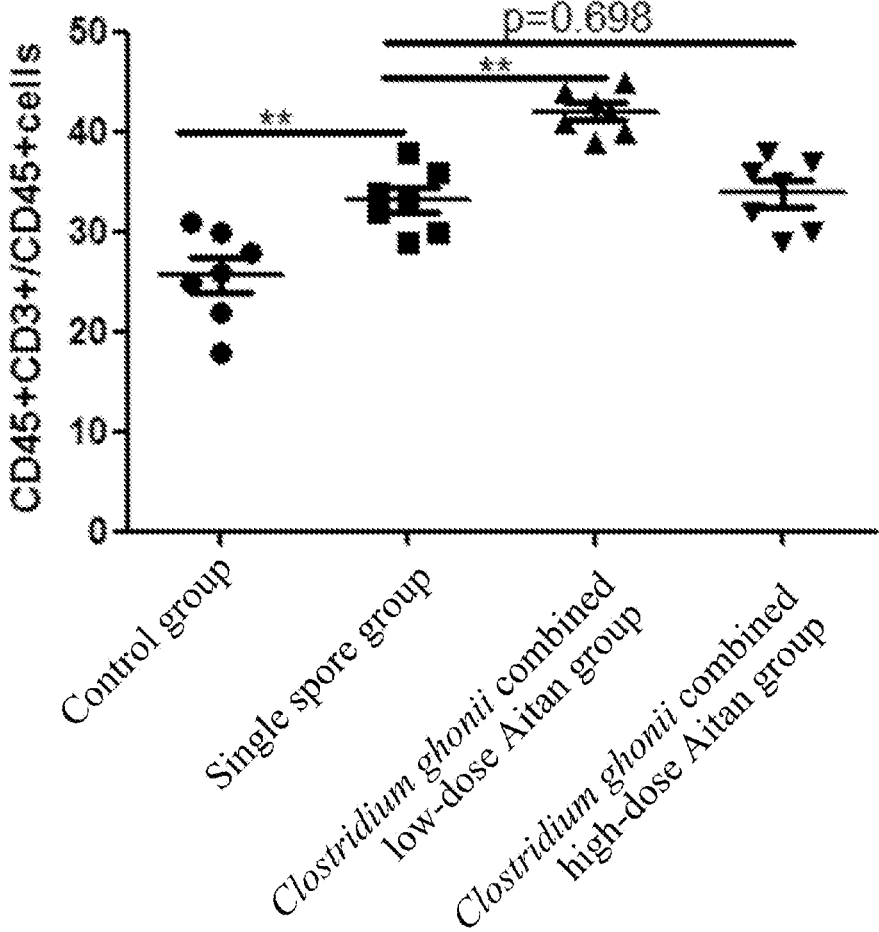
FIGS. 10A-C show proportions of infiltrating T cells in tumor tissues in example 4.
Figure 10B:
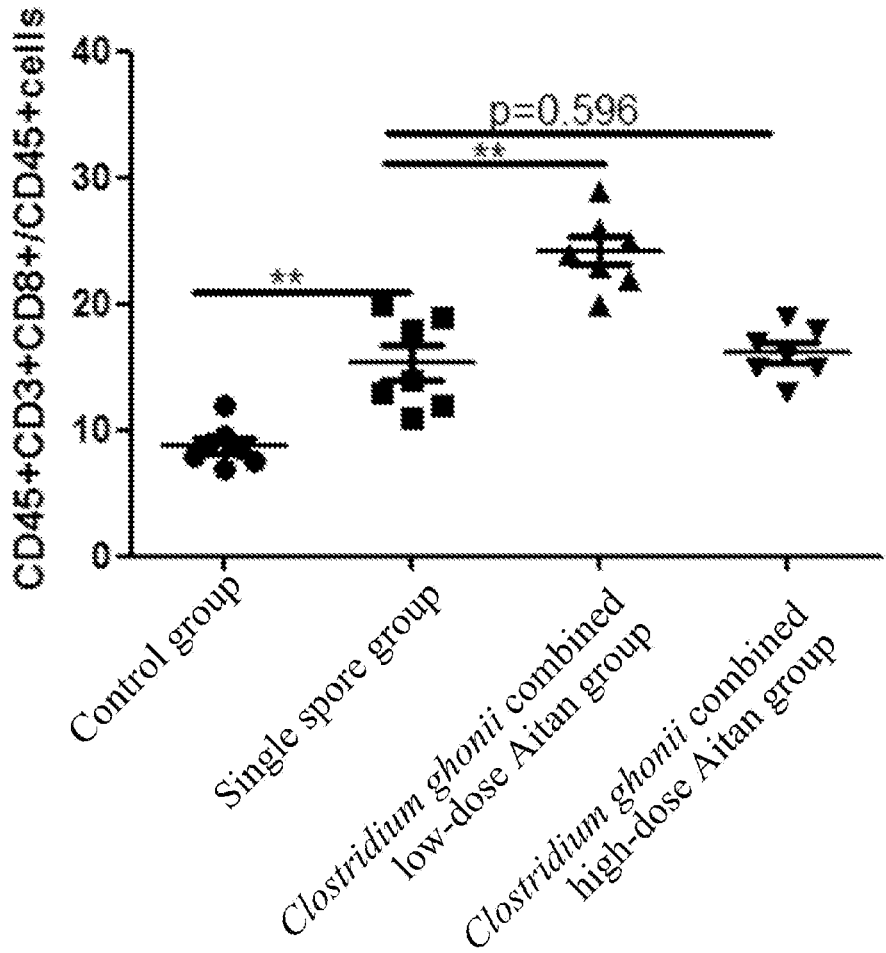
Figure 10C:
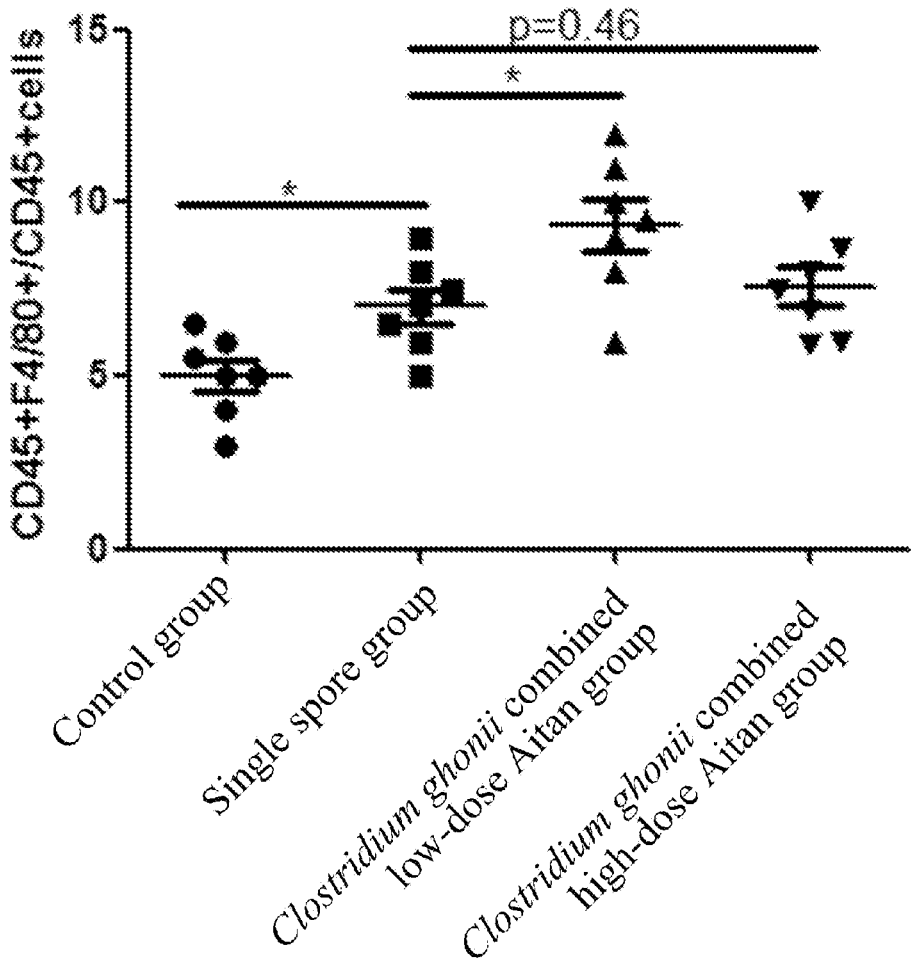

The tumor tissues of the mice treated in the control group, the single spore group, the *Clostridium ghonii* combined low-dose apatinib (AITAN) group and the *Clostridium ghonii* combined high-dose apatinib (AITAN) group were separately taken and subjected to a flow cytometry by a flow cytometer. Compared with the control group, a proportion of tumor-infiltrating $CD45^+CD3^+$ T, $CD45^+CD3^+CD8^+$ T and $F4/80^+$ cells in the tumor tissues was significantly increased in the single spore group, the *Clostridium ghonii* combined low-dose apatinib (AITAN) group and the *Clostridium ghonii* combined high-dose apatinib (AITAN) group; and compared with the single spore group, a proportion of tumor-infiltrating $CD45^+CD3^+$ T, $CD45^+CD3^+CD8^+$ T and $F4/80^+$ cells in the tumor tissues was significantly increased in the *Clostridium ghonii* combined low-dose apatinib (AITAN) group, but showed no significant difference in the *Clostridium ghonii* combined high-dose apatinib (AITAN) group (FIGS. 10A-C).

Figure 11A:
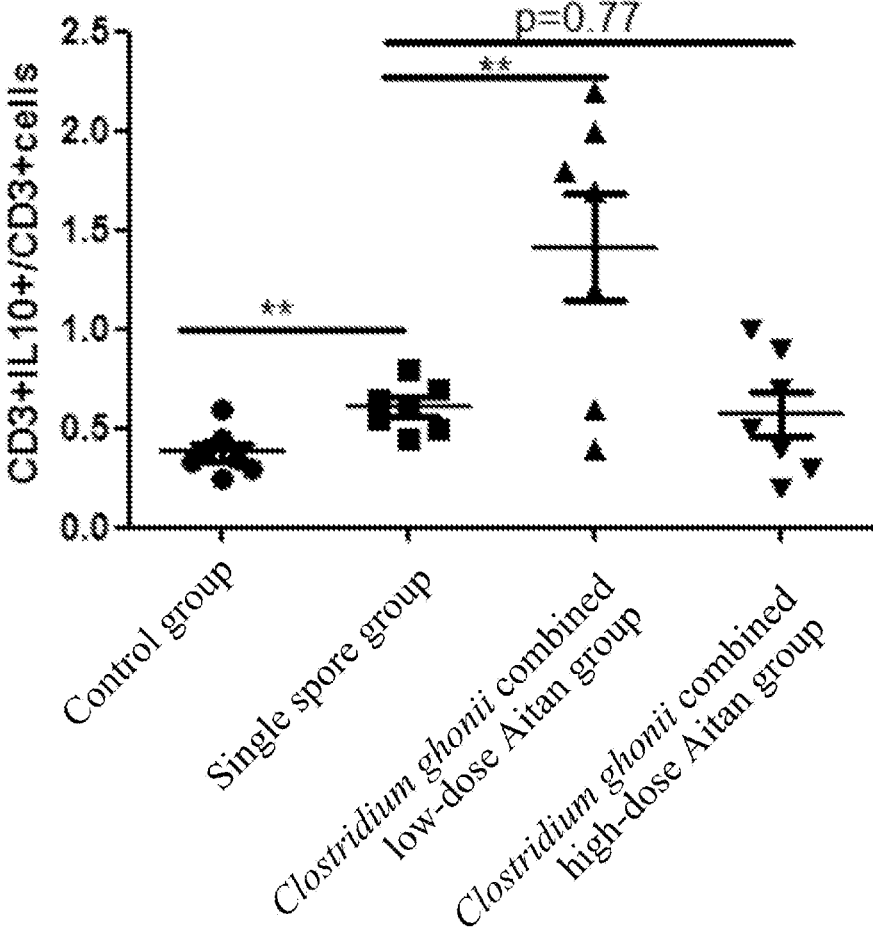
FIGS. 11A-B show expressions of cytokines of T cells in tumor tissues.
Figure 11B:
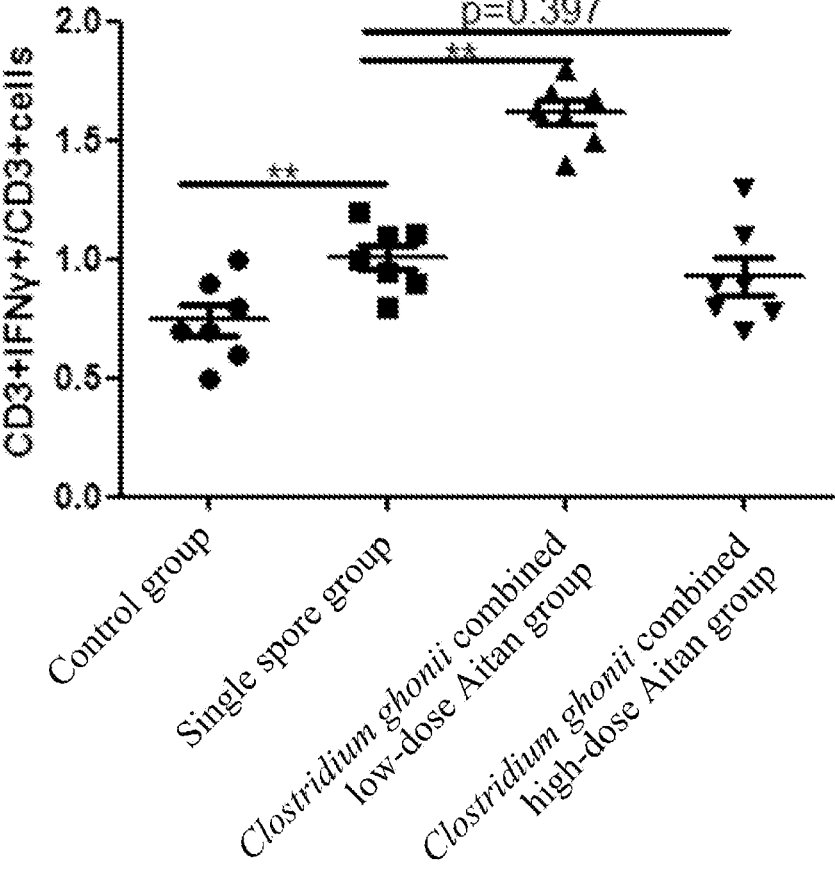
Figure 12A:
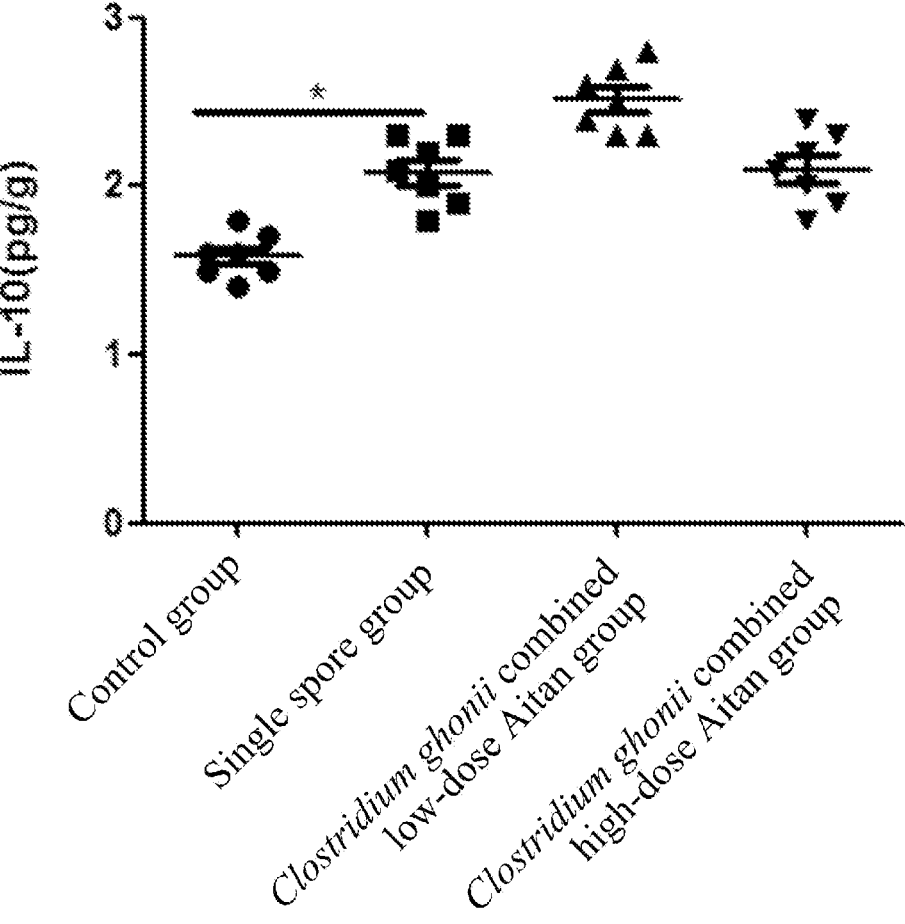
FIGS. 12A-D show expressions of cytokines in mouse tumors in example 4.
Figure 12B:
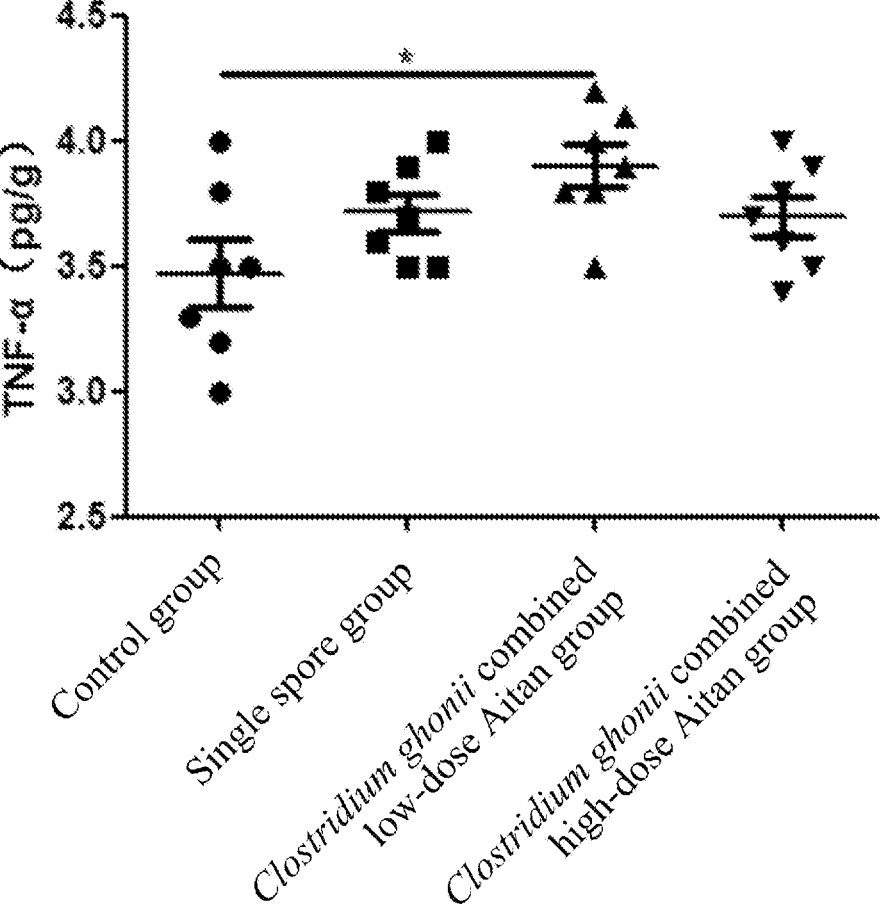
Figure 12C:
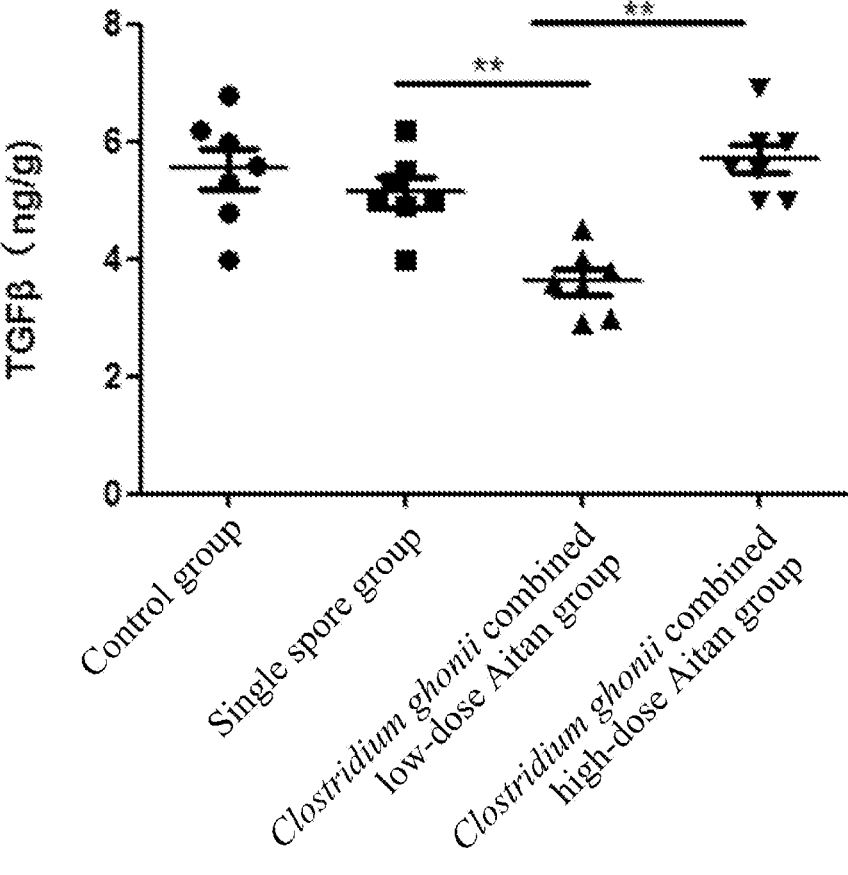
Figure 12D:
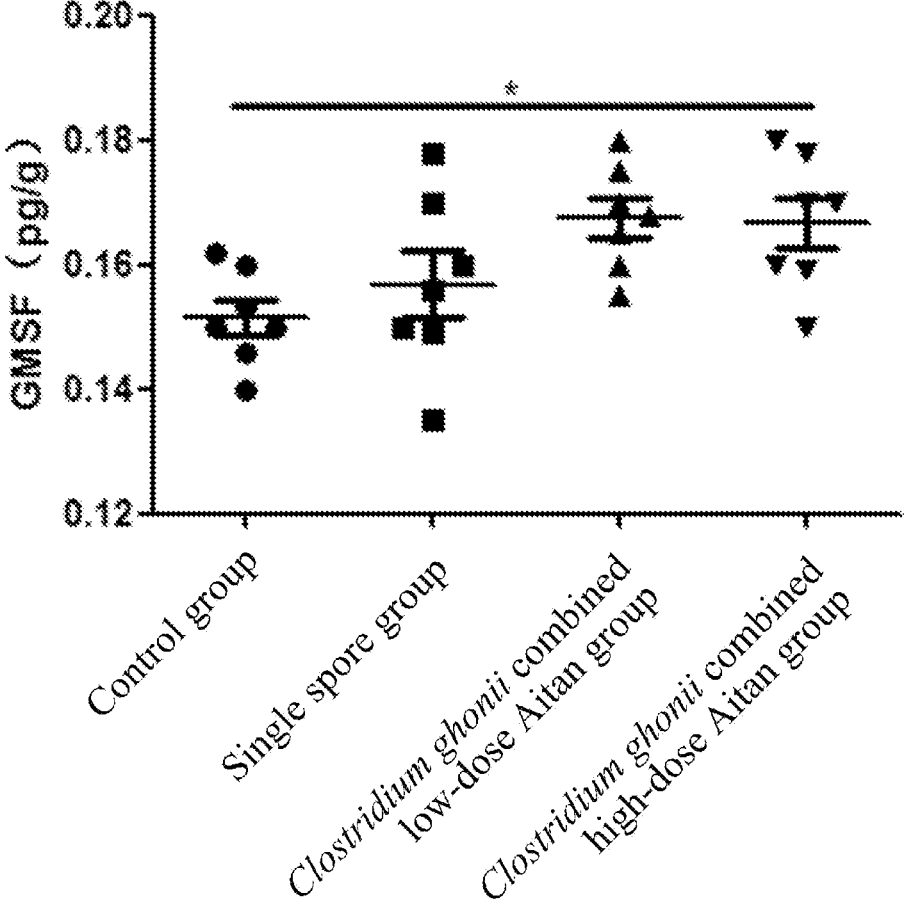

Expressions of cytokines of T cells in the tumors were investigated by intracellular staining. Compared with the single spore group, $CD3^+$ IL-$10^+$ T cells and $CD3^+$ IFN-$\gamma^+$ T cells in the tumors were significantly increased in the *Clostridium ghonii* combined low-dose apatinib (AITAN) group (p<0.05), while the $CD3^+$ IL-$10^+$ T cells and $CD3^+$ IFN-$\gamma^+$ T cells showed no significant change in the *Clostridium ghonii* combined high-dose apatinib (AITAN) group (FIGS. 11A-B).

Intratumoral cytokines such as IL-10, TNF-α, GM-CSF and TGFβ were detected by Multi-ELISA. Compared with the control group, the IL-10, the TNF-α and the GM-CSF were all increased in the single spore group, the *Clostridium ghonii* combined high-dose apatinib (AITAN) group and the *Clostridium ghonii* combined low-dose apatinib (AITAN) group. Compared with other groups, the expression of the TGFβ in the tumors of the *Clostridium ghonii* combined low-dose apatinib (AITAN) group was significantly decreased (FIGS. 12A-D). It can be seen that oncolysis by *Clostridium ghonii* can induce expressions of the cytokines and chemokines in TME. At the same time, the *Clostridium ghonii* combined with the low-dose apatinib (AITAN) can significantly reduce the expression of the TGFβ and relieve the immunosuppressive tumor microenvironment. But the combination with high-dose apatinib (AITAN) had no obvious inhibitory effect on the expression of the TGFB.

Figure 13A:
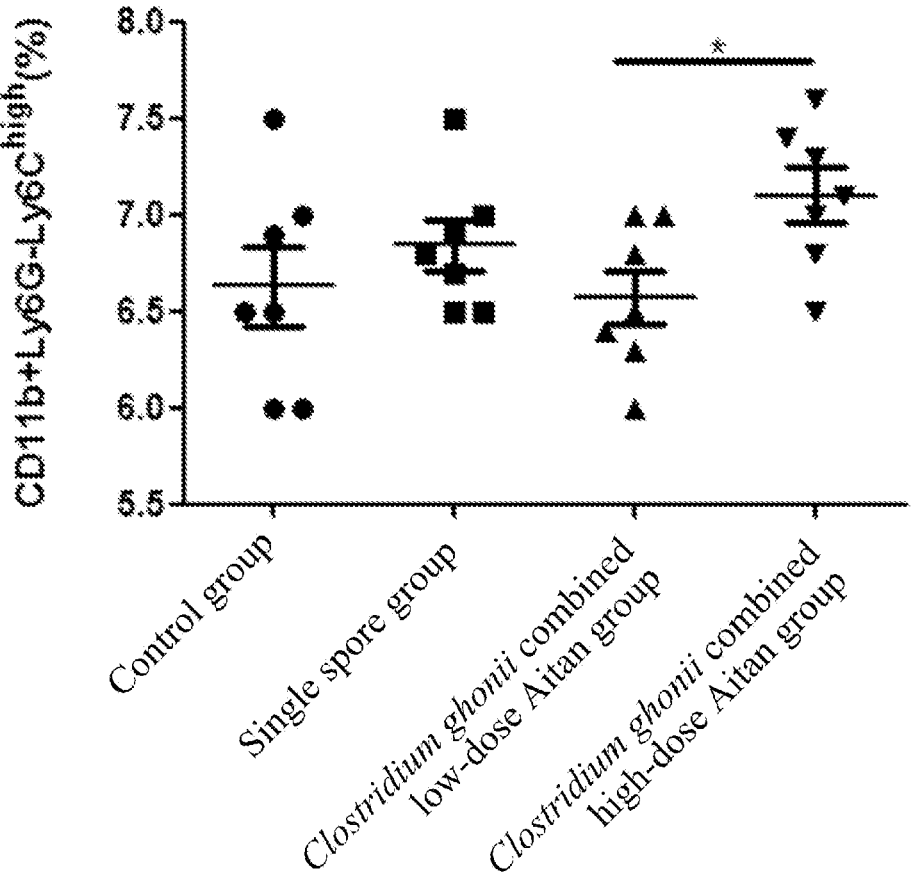
FIGS. 13A-B and 14 show proportions of myeloid-derived suppressor cells (MDSCs) and tumor-associated macrophages (TAMs) in mouse tumors in example 4.
Figure 13B:
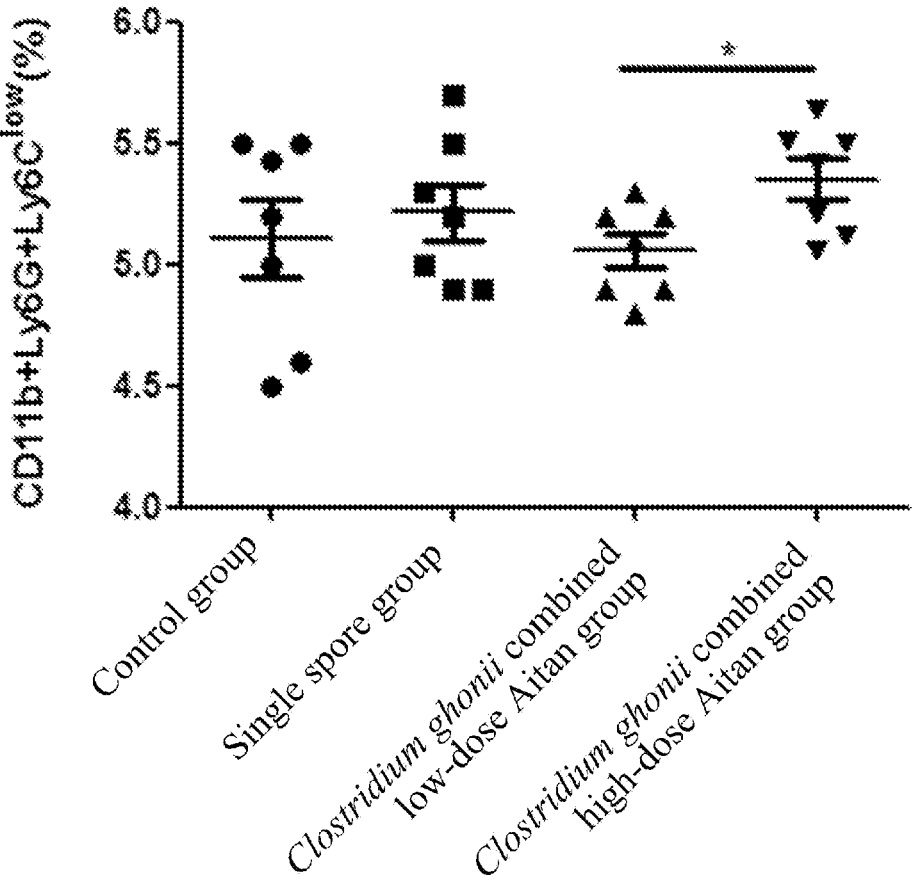
Figure 14:
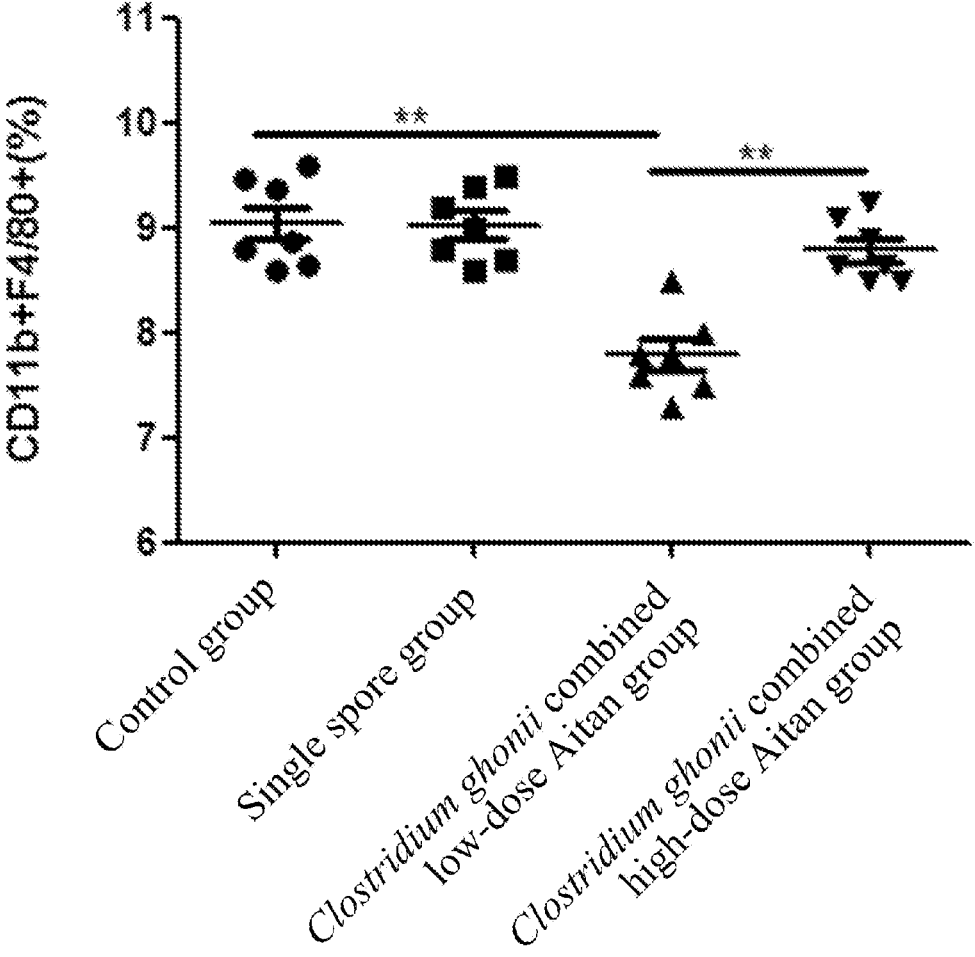
Figure 15A:
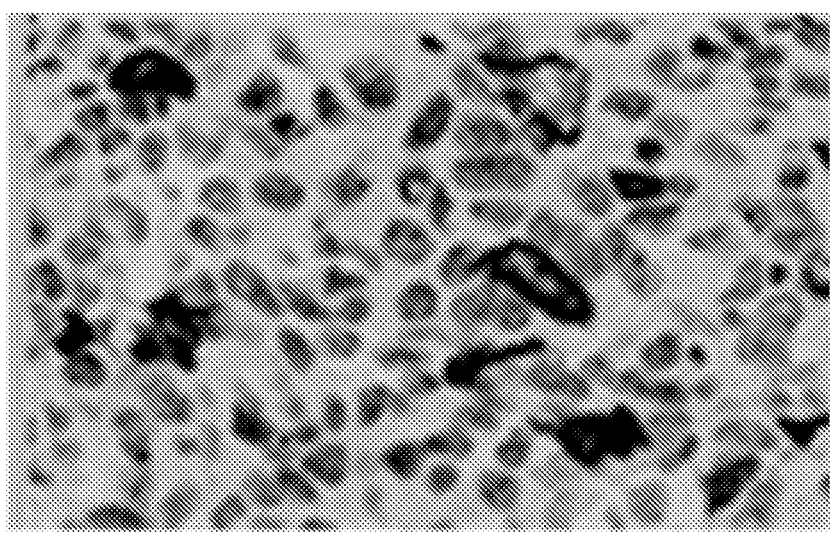
FIGS. 15A-D and FIGS. 16A-C are immunohistochemistry staining images of mouse tumor tissues and a graph showing a proportion of CD163 cells in example 4.
Figure 15B:
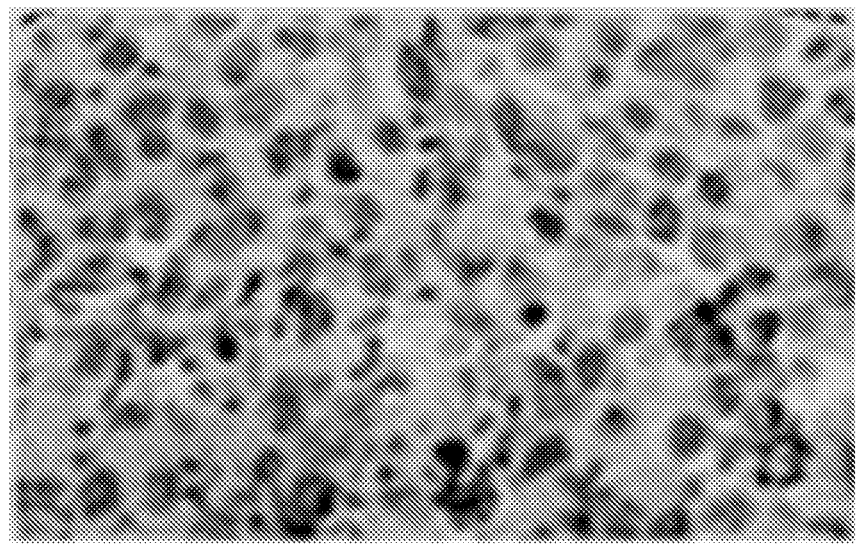
Figure 15C:
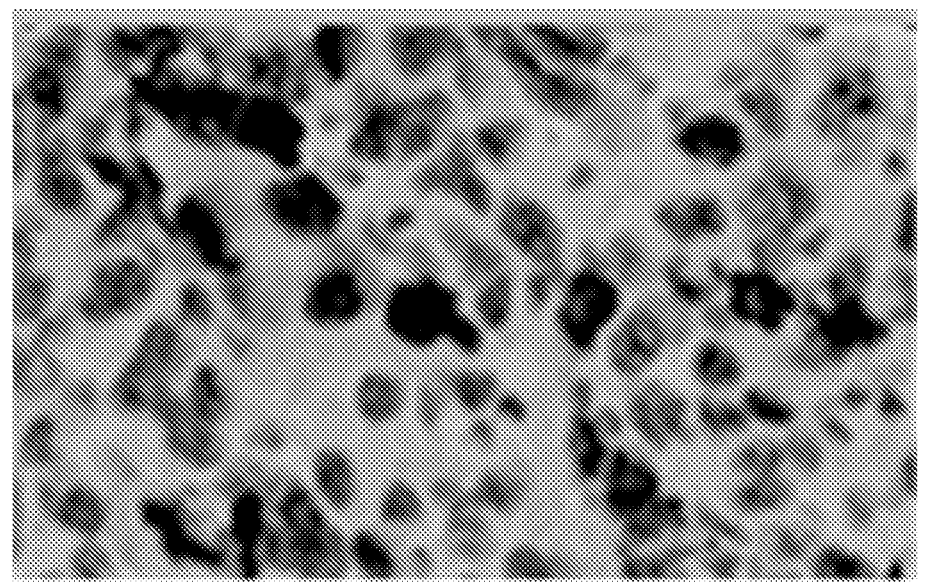
Figure 15D:
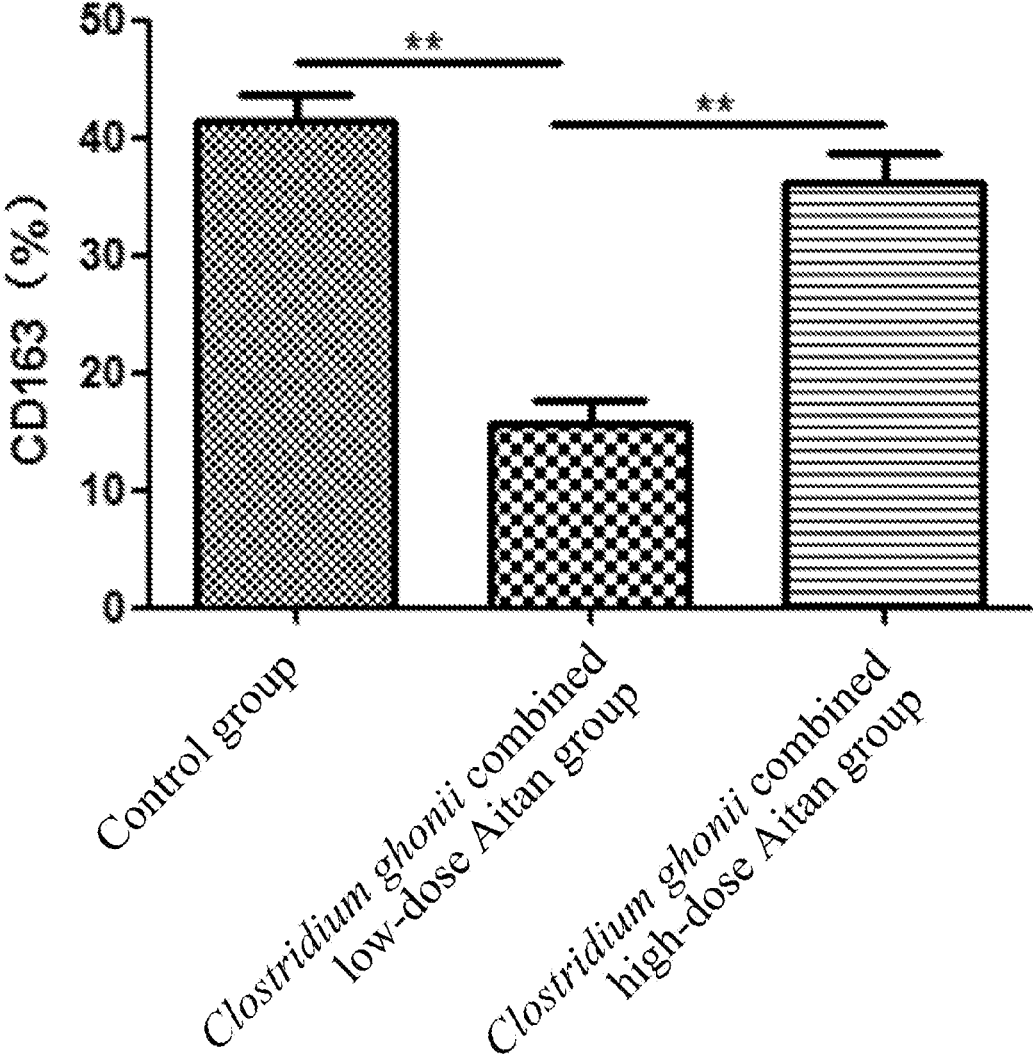

The number of myeloid-derived suppressor cells (MD-SCs) and tumor-associated macrophages (TAMs) in tumors was analyzed by flow cytometry. Compared with the control group, the number of intratumoral $CD11b^+$ Ly6G$^-$ Ly6C$^{high}$ mononuclear MDSCs (Mo-MDSCs) and $CD11b^+Ly6G^+$ Ly6C$^{low}$ polymorphonuclear-MDSCs (PMN-MDSCs) was not significantly different in the *Clostridium ghonii* combined low-dose apatinib (AITAN) group. Compared with the *Clostridium ghonii* combined high-dose apatinib (AITAN) group, proportions of the Mo-MDSCs and the PMN-MDSCs were decreased in the *Clostridium ghonii* combined low-dose apatinib (AITAN) group (FIGS. 13A-B). In addition, a proportion of $CD11b^+F4/80^+$-TAMs in total viable cells was significantly decreased in the *Clostridium ghonii* combined low-dose apatinib (AITAN) group compared with other treatment groups (FIG. 14). CD163$^+$ (M2-like macrophage marker) in the tumors was detected by IHC staining. The results showed that the number of the CD163+ cells in the tumors of the *Clostridium ghonii* combined low-dose apatinib (AITAN) group decreased, indicating that the *Clostridium ghonii* combined with the low-dose apatinib (AITAN) can effectively reduce the number of TAMs in the tumors (FIGS. 15A-D).

Figure 16A:
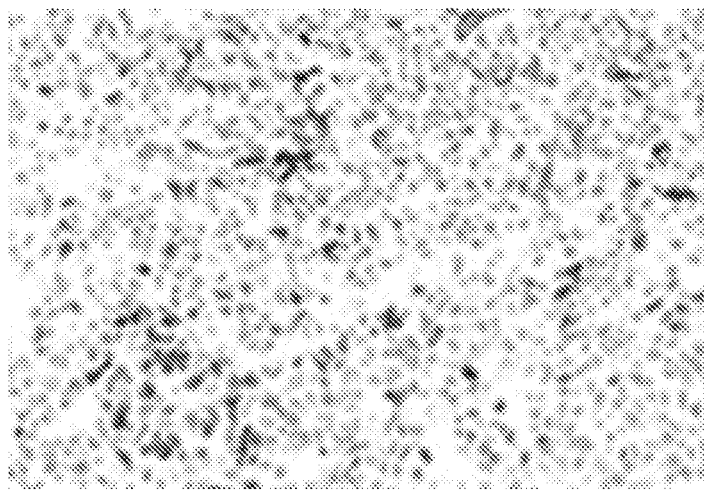
Figure 16B:
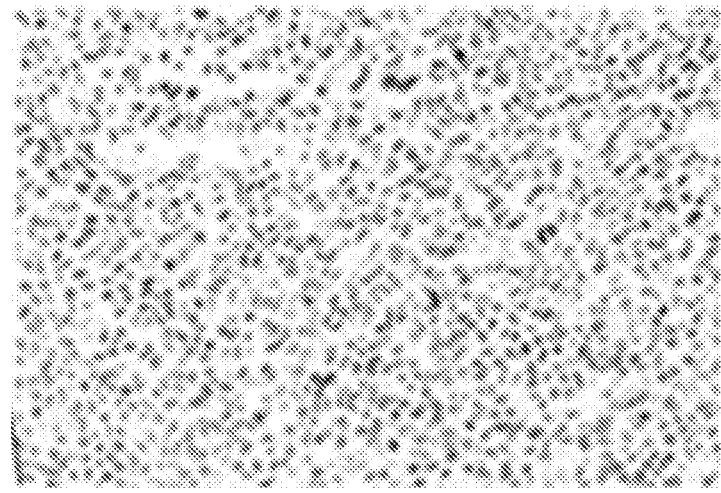
Figure 16C:
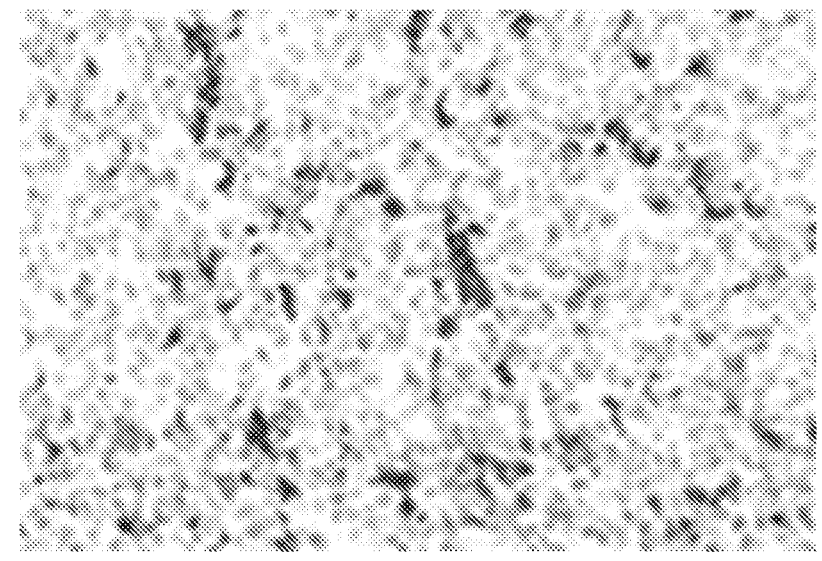

HIF-$1\alpha$ immunohistochemistry staining of the tumor tissues showed that compared with the control group, hypoxia was significantly reduced in the tumor tissues of the *Clostridium ghonii* combined low-dose apatinib (AITAN) group, but increased in the tumor tissues of the *Clostridium ghonii* combined high-dose apatinib (AITAN) group (FIGS. 16A-C). The results showed that the high-dose apatinib (AITAN) aggravated the hypoxia of the tumor tissues. Although a hypoxic environment conducive to reproduction of *Clostridium ghonii* was created, an anti-tumor effect of the *Clostridium ghonii* combined high-dose apatinib (AITAN) group was lower than that of the *Clostridium ghonii* combined low-dose apatinib (AITAN) group. However, although the tumor hypoxia in the *Clostridium ghonii* combined low-dose apatinib (AITAN) group was significantly reduced, tumor growth could be theoretically accelerated, but the tumor volume showed that the tumor growth was significantly inhibited.

In conclusion, the *Clostridium ghonii* combined with the low-dose apatinib (AITAN) can promote infiltration of $CD45^+CD3^+$ T, $CD45^+CD3^+CD8^+$ T, $F4/80^+$ and other immune cells, induces enhanced expressions of IFN-γ, TNF-α, GM-CSF and other cytokines and chemokines, effectively reduces an expression of TGFβ in tumor tissues and the number of immunosuppressive agents of tumor-associated macrophages (TAM), myeloid-derived suppressor cells (MDSCs), etc., and reduces immunosuppression. It can be seen that the *Clostridium ghonii* combined with low-dose apatinib (AITAN) highly effectively prevents against tumors by inducing tumor vascular normalization, converts an immunosuppression state of the TME into an immune activation state. A unique treatment effect is attributed to a change of an anti-tumor immune microenvironment instead of creating an anoxic environment for breeding *Clostridium ghonii* by high-dose apatinib (AITAN) to aggravate tumor hypoxia.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A pharmaceutical product for treating a tumor, comprising a *Clostridium ghonii* combined with apatinib, wherein every $1 \times 10^7$ Colony Forming Units (CFU) of the *Clostridium ghonii* in a spore form is combined with the apatinib at a dose of 60 mg/kg/d.

2. The pharmaceutical product according to claim 1, wherein the *Clostridium ghonii* is a *Clostridium ghonii* MW-DCG-LCv-26 strain; and the *Clostridium ghonii* MW-DCG-LCv-26 strain is deposited in the National Measurement Institute, Australia and has a date of deposit of Apr. 18, 2012 and a deposit number of V12/001486.

3. The pharmaceutical product according to claim 1, wherein the tumor is colon cancer, Lewis lung carcinoma, nasopharyngeal cancer, non-small cell lung cancer, fibrosarcoma, or melanoma.

4. The pharmaceutical product according to claim 1, wherein the *Clostridium ghonii* is a *Clostridium ghonii* spore freeze-dried powder.

5. The pharmaceutical product according to claim 4, wherein the *Clostridium ghonii* spore freeze-dried powder has a specification of $1 \times 10^8$ CFU/bottle.

6. A method for treating a tumor, wherein *Clostridium ghonii* is administered in combination with apatinib;

the *Clostridium ghonii* is in a spore form; a subject is intratumorally administered with the apatinib once every day for 3 days and then *Clostridium ghonii* spores at a dose of $1 \times 10^7$ Colony Forming Units (CFU)/tumor/time once every other day for a total of two times; and the apatinib is gavaged at a dose of 60 mg/kg/d or 120 mg/kg/d or 180 mg/kg/d.

* * * * *